US010035145B2

(12) United States Patent
McClelland et al.

(10) Patent No.: US 10,035,145 B2
(45) Date of Patent: Jul. 31, 2018

(54) PISTON ASSEMBLY AND RELATED SYSTEMS FOR USE WITH A FLUIDICS DEVICE

(71) Applicant: SciKon Innovation, Inc., Chapel Hill, NC (US)

(72) Inventors: Randall Edwin McClelland, Chapel Hill, NC (US); Maureen Kay Bunger, Morrisville, NC (US); Frank Jay Ziberna, Winfield, IL (US)

(73) Assignee: SciKon Innovation, Inc., Chapel Hill, NC (US)

( * ) Notice: Subject to any disclaimer, the term of this patent is extended or adjusted under 35 U.S.C. 154(b) by 429 days.

(21) Appl. No.: 14/954,546

(22) Filed: Nov. 30, 2015

(65) Prior Publication Data

US 2016/0151778 A1 Jun. 2, 2016

Related U.S. Application Data

(60) Provisional application No. 62/086,623, filed on Dec. 2, 2014.

(51) Int. Cl.
*B01L 3/00* (2006.01)
*C12M 1/26* (2006.01)
(Continued)

(52) U.S. Cl.
CPC ................ *B01L 3/502* (2013.01); *F04B 1/00* (2013.01); *F04B 13/00* (2013.01); *F04B 23/025* (2013.01);
(Continued)

(58) Field of Classification Search
CPC .. B01L 3/502; B01L 3/0217; B01L 2200/025; B01L 2200/026;
(Continued)

(56) References Cited

U.S. PATENT DOCUMENTS

| | | | |
|---|---|---|---|
| D246,466 | S | 11/1977 | Attree et al. |
| 4,239,853 | A | 12/1980 | Bradley |

(Continued)

FOREIGN PATENT DOCUMENTS

| | | | |
|---|---|---|---|
| GB | 2147100 | A | 5/1985 |
| WO | WO2011137039 | A1 | 11/2011 |

OTHER PUBLICATIONS

USPTO, Notice of Allowance for Design U.S. Appl. No. 29/465,155, dated May 4, 2016.

(Continued)

*Primary Examiner* — Michael L Hobbs
(74) *Attorney, Agent, or Firm* — Forrest Firm, P.C.

(57) ABSTRACT

Disclosed are fluidics devices and assemblies allowing for fluid flow between a plurality of wells. The fluidics devices and assemblies that are provided mimic in vivo tissue environments by allowing for initially segregated tissue cultures that can then be linked through fluid flow to measure integrated tissue response. The fluidics devices and assemblies provide a pumpless system using surface tension, gravity, and channel geometries. By linking human tissue functional systems to better simulate in vivo feedback and response signals between the tissues, the need for testing in animals can be minimized. Further, piston assemblies and related systems are provided for nesting engagement on top of the fluidics device in order to provide a dosing fluid thereto.

26 Claims, 24 Drawing Sheets

(51) Int. Cl.

| | |
|---|---|
| ***F04B 53/00*** | (2006.01) |
| ***F04B 23/02*** | (2006.01) |
| ***F04B 53/14*** | (2006.01) |
| ***F04B 1/00*** | (2006.01) |
| ***F04B 13/00*** | (2006.01) |
| *B01L 3/02* | (2006.01) |

(52) U.S. Cl.
CPC ............ *F04B 53/006* (2013.01); *F04B 53/14* (2013.01); *B01L 3/0217* (2013.01); *B01L 2200/025* (2013.01); *B01L 2200/026* (2013.01); *B01L 2200/0642* (2013.01); *B01L 2300/069* (2013.01); *B01L 2300/0829* (2013.01); *B01L 2400/0457* (2013.01)

(58) Field of Classification Search
CPC ....... B01L 2200/0642; B01L 2300/069; B01L 2300/0829; B01L 2400/0457; F04B 13/00; F04B 23/025; F04B 1/00; B04B 53/006; B04B 53/14
See application file for complete search history.

(56) References Cited

U.S. PATENT DOCUMENTS

| | | | |
|---|---|---|---|
| D264,810 | S | 6/1982 | Voltmann |
| D271,239 | S | 11/1983 | Lemieux et al. |
| 4,483,925 | A | 11/1984 | Noack |
| D284,699 | S | 7/1986 | Jolley |
| D288,484 | S | 2/1987 | Mitchell |
| D302,207 | S | 7/1989 | Matkovich |
| D303,149 | S | 8/1989 | Andersen |
| 5,130,105 | A | 7/1992 | Carter et al. |
| D335,348 | S | 5/1993 | Frenkel et al. |
| 5,417,923 | A | 5/1995 | Bojanic et al. |
| 5,487,872 | A | 1/1996 | Hafeman et al. |
| 5,588,441 | A | 12/1996 | Fishman |
| 5,801,055 | A | 9/1998 | Henderson |
| 5,817,510 | A | 10/1998 | Pandey et al. |
| D404,497 | S | 1/1999 | Lahm et al. |
| D411,308 | S | 6/1999 | Pandey et al. |
| 5,993,745 | A | 11/1999 | Laska |
| D420,743 | S | 2/2000 | Monks |
| 6,019,225 | A | 2/2000 | Kalmakis et al. |
| 6,106,783 | A | 8/2000 | Gamble |
| 6,395,234 | B1 | 5/2002 | Hunnell et al. |
| 6,439,884 | B1 | 8/2002 | Cronin |
| 6,485,690 | B1 | 11/2002 | Pfost et al. |
| D469,544 | S | 1/2003 | Lafond et al. |
| 6,632,656 | B1 | 10/2003 | Thomas et al. |
| 6,637,463 | B1 | 10/2003 | Lei et al. |
| 6,875,405 | B1 | 4/2005 | Mathus et al. |
| 6,939,709 | B2 | 9/2005 | Henderson et al. |
| 6,987,253 | B2 | 1/2006 | Bedingham et al. |
| 7,005,029 | B2 | 2/2006 | Khan et al. |
| 7,279,134 | B2 | 10/2007 | Chan et al. |
| D574,505 | S | 8/2008 | Muller-Cohn et al. |
| 7,452,510 | B2 | 11/2008 | Weinfield et al. |
| 7,560,073 | B1 | 7/2009 | Peters et al. |
| D632,803 | S | 2/2011 | Motadel et al. |
| 7,922,672 | B2 | 4/2011 | Hein, Jr. et al. |
| D672,053 | S | 12/2012 | Chen et al. |
| 8,377,685 | B2 | 2/2013 | Meyvantsson et al. |
| D699,370 | S | 2/2014 | Motadel et al. |
| D699,859 | S | 2/2014 | Motadel |
| D720,468 | S | 12/2014 | Calderwood et al. |
| D724,236 | S | 3/2015 | Motadel et al. |
| D730,537 | S | 5/2015 | Burroughs et al. |
| 2003/0138941 | A1 | 7/2003 | Gong et al. |
| 2004/0101439 | A1 | 5/2004 | Fusco et al. |
| 2005/0072030 | A1 | 4/2005 | Wu |
| 2005/0147958 | A1 | 7/2005 | Hassanein et al. |
| 2006/0093530 | A1 | 5/2006 | Ueda |
| 2006/0137434 | A1 | 6/2006 | Cohen et al. |
| 2007/0166816 | A1 | 7/2007 | Campbell et al. |
| 2008/0060424 | A1 | 3/2008 | Babic et al. |
| 2009/0023610 | A1 | 1/2009 | Peytavi |
| 2010/0041143 | A1 | 2/2010 | Nishiyama et al. |
| 2010/0233694 | A1 | 9/2010 | Kopf-Sill |
| 2010/0284859 | A1 | 11/2010 | Cooney et al. |
| 2011/0236278 | A1 | 9/2011 | Motadel et al. |
| 2012/0135452 | A1 | 5/2012 | Shuler et al. |
| 2012/0328488 | A1 | 12/2012 | Puntambekar et al. |

OTHER PUBLICATIONS

USPTO, Non-Final Rejection for U.S. Appl. No. 14/016,913, dated May 13, 2016.

Inamdar NK.; Borenstein JT.; Microfluidic cell culture models for tissue engineering, Current Opinion in Biotechnology, 2011, 22, 1-9.

Domanksy K.; Inman W.; Serdy J.; Dash A.; Lim M.; Griffith L.; Perfused multiwell plate for 3D liver tissue engineering, Lab Chip, 2010, 10, 51-58.

Dance A, Enter the Third Dimension, Cell culture goes 3-D with devices that better mimic in vivo conditions, The Scientist, Sep. 1, 2012.

Keenan T & Folch A, Biomolecular gradients in cell culture systems, Lab Chip, 2008, 8, 34-57.

ISA/KR, International Search Report and Written Opinion for PCT Patent Application No. PCT/US2016/023844, dated Jul. 25, 2016.

Toh, Yi-Chin et al., "A microfluidic 3D hepatocyte chip for drug toxicity testing", Lab on a Chip, 2009, vol. 9, No. 14, pp. 2026-2035.

Ye, Nannan et al., "Cell-based high content screening using an integrated microfluidic device", Lab on a Chip, 2007, vol. 7, No. 12, pp. 1696-1704.

Kim, Jeongyun et al., "A programmable microfluidic cell array for combinatorial drug screening", Lab on a Chip, 2012, vol. 12, No. 10, pp. 1813-1822.

USPTO, Notice of Allowance for U.S. Appl. No. 14/016,913, dated Dec. 22, 2016.

USPTO, Final Rejection for U.S. Appl. No. 14/016,913, dated Nov. 16, 2016.

PISTON ASSEMBLY AND RELATED SYSTEMS FOR USE WITH A FLUIDICS DEVICE

CROSS-REFERENCE TO RELATED APPLICATIONS

This application is a non-provisional of U.S. Provisional Patent Application No. 62/086,623 filed Dec. 2, 2014, which is incorporated herein by reference in its entirety.

TECHNICAL FIELD

This disclosure is related to a piston assembly and related systems for use with a fluidics device for providing a dosing fluid thereto and allowing fluid flow between a plurality of wells.

BACKGROUND

It is estimated to cost on the order of $1B dollars to bring a drug candidate to market and the pharmaceutical industry is enhancing its chances of success by investing in human pre-clinical research. This money has driven the absorption, distribution, metabolism, elimination, and toxicology (ADMET) market in human-based products to a $5 billion dollar annual industry. The current technology for testing drug candidates is based on homogeneous culture techniques and animal models. Thus, there is an unmet need for biotool devices capable of linking human tissue functional systems to better simulate in vivo feedback and response signals between tissues and to minimize testing in animals.

Accordingly, such biotool devices and assemblies are provided in the present disclosure.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein is a fluidics device for allowing fluid flow between a plurality of wells. The fluidics device includes a dosing well positioned upstream from a plurality of wells for containing a respective host fluid and one or more channels extending between adjacent upstream and downstream wells to define a channel fluid flow path there between, such that a dosing fluid deposited into the dosing well flows to the respective host fluid of the adjacent downstream well along the channel fluid flow path there between, and the respective host fluid subsequently flows to each adjacent downstream well along the channel fluid flow path there between.

According to one or more embodiments, the fluidics device can include a wick downstream from at least a portion of the plurality of wells. The wick is in fluid contact with the channel fluid flow path for regulating fluid flow through the plurality of wells.

According to one or more embodiments, the fluidics device can include a collection well downstream from the plurality of wells to collect the respective host fluid after having flowed through the plurality of wells. The collection well of the fluidics device can define an aperture, wherein the aperture is defined at a lower portion of a floor of the collection well.

According to one or more embodiments, the wick can be contained in the collection well such that the wick is in fluid contact with the channel fluid flow path for regulating fluid flow through the plurality of wells.

According to one or more embodiments, the surface of one or more of the plurality of wells of the fluidics device can be modified with one or both of a chemical layer or a protein layer to support a cell culture. The protein layer for supporting the cell cultures can include one or more of collagen I, collagen II, collagen III, laminin, or fibronection, or combinations thereof.

Disclosed herein is an assembly for allowing fluid flow between a plurality of wells. The assembly includes one or more fluidics devices nestably engaged and one or more reservoir trays nestably engaged on top of the fluidics device(s). The reservoir tray includes at least one chamber for containing a respective chamber fluid and an aperture defined in the chamber floor and configured such that the aperture is positioned above a dosing well of the fluidics device when in nesting engagement with the fluidics device. The floor of the chamber is angled and the aperture is defined at a lower portion of the chamber floor such that the chamber fluid flows through the aperture into the dosing well when the reservoir tray and the fluidics device are nestably engaged.

According to one or more embodiments, the assembly can include one or more reservoir trays nestably engaged underneath the fluidics device(s). The fluidics device can include a collection well downstream from the plurality of wells and the collection well defines an aperture such that fluid from the collection well flows through the aperture into the chamber of the reservoir tray nestably engaged underneath the fluidics device(s).

According to one or more embodiments, the assembly can further include a cover tray configured for nesting engagement on top of the reservoir tray nestably engaged on top of the fluidics device.

Disclosed herein is a piston assembly for providing a dosing fluid to a fluidics device. The piston assembly includes a reservoir tray configured for nesting engagement with a fluidics device. The reservoir tray includes a liquid chamber defining a chamber floor for containing a dosing fluid, and an aperture defined in the chamber floor and positioned above a dosing well of the fluidics device when the reservoir tray is nestably engaged with the fluidics device. The chamber floor of the reservoir tray is angled and the aperture is defined at a lower portion of the chamber floor such that the dosing fluid flows through the aperture into the dosing well of the fluidics device when the reservoir tray and the fluidics device are nestably engaged. Further, the piston assembly includes a reservoir cover defining a piston chamber that receives at least a portion of a piston for allowing the piston to translate between a first position a distance from the aperture and a second position proximal to the aperture. Additionally, the piston assembly includes a crank engaged with the piston for translating the piston between the first position and the second position such that the translation from the first position to the second position results in a portion of the dosing fluid flowing through the aperture to the dosing well when the reservoir tray and the fluidics device are nestably engaged.

Disclosed herein is also a piston assembly for providing fluid to a fluidics device with more than one dosing well. The piston assembly includes a reservoir tray configured for nesting engagement with a fluidics device and including a chamber defining a chamber floor and dividing walls creating subchambers for housing a dosing fluid include an aperture defined in the chamber floor and positioned above a dosing well of the fluidics device when the reservoir tray is nestably engaged with the fluidics device. The chamber floor of each subchamber is angled and the aperture is defined at a lower portion of the chamber floor such that the dosing fluid flows through the aperture into the dosing well of the fluidics device when the reservoir tray and the fluidics device are nestably engaged. The piston assembly further includes a reservoir cover defining a chamber housing a piston for each of subchambers for allowing the piston to translate a between a first position a distance from the aperture and a second position proximal to the aperture. Additionally, the piston assembly includes a crank assembly engaged with the pistons for translating the pistons such that a portion of the dosing fluid flows through the aperture when the reservoir tray and the fluidics device are nestably engaged.

According to one or more embodiments, the aperture of the piston assembly can define one or more openings, the one or more openings configured for communication with fluid in the liquid chamber such that surface tension of the fluid maintains the fluid in the liquid chamber until the piston is translated from the first position to the second position.

According to one or more embodiments, the piston chamber of the piston assemblies can define a chamber lip for engaging with a piston catch defined by the piston, thereby retarding the translation of the piston when the piston translates from the second position to the first position.

According to one or more embodiments, the reservoir cover of the piston assemblies can define a cover lip for engaging with a crank catch defined by the crank, thereby retarding the translation of the crank when the piston is translating from the second position to the first position.

According to one or more embodiments, the chamber floor of the piston assemblies can define a piston well including the aperture for receiving the piston in the second position and the dosing fluid.

According to one or more embodiments, the piston well of the piston assemblies can include a piston well wall for nestably engaging at least half of the circumference of the piston during the entire translation between the first position and the second position and for delivering the dosing fluid to the piston well.

According to one or more embodiments, the chamber floor of the piston assemblies can define a floor recess at the lower portion of the chamber floor proximal to the piston well and the piston well wall for receiving the dosing fluid and delivering the dosing fluid to the piston recess.

According to one or more embodiments, the crank of the piston assemblies can include a pin engaged within a piston channel defined in the piston for engaging the crank to the piston.

According to one or more embodiments, the crank of the piston assemblies are in communication with a solenoid.

BRIEF DESCRIPTION OF THE DRAWINGS

This application is related to the subject matter of U.S. Provisional Application 61/697,395 filed Sep. 6, 2012, U.S. application Ser. No. 14/016,913 filed Sep. 3, 2013, and U.S. Provisional Application No. 62/136,911 filed Mar. 23, 2015, each of which is incorporated by reference herein in its entirety.

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

Figure 1:
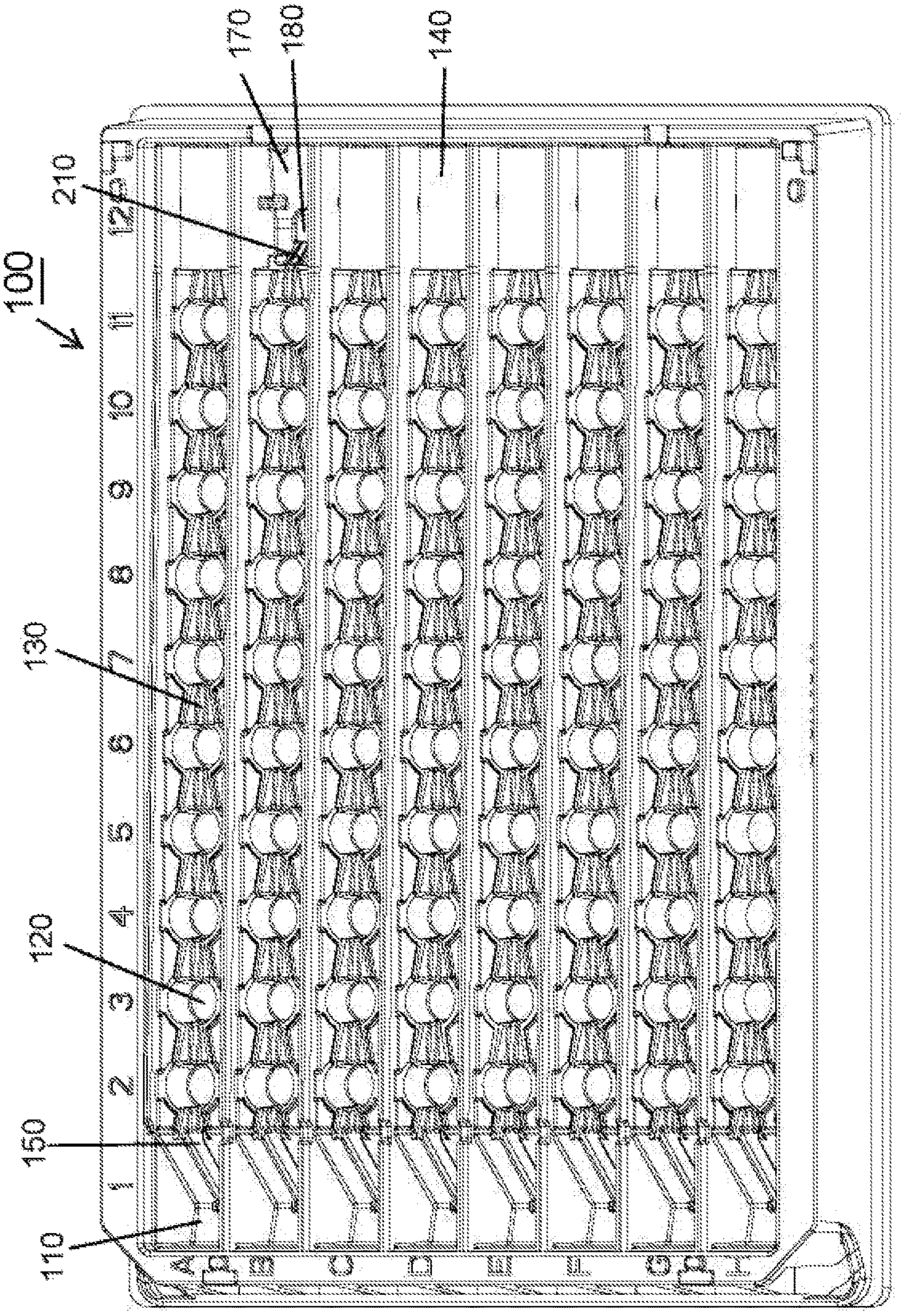
FIG. 1 is a perspective view of a fluidics device in accordance with embodiments of the present disclosure.

The presently disclosed subject matter provides fluidics devices and assemblies that in one aspect are capable of linking functional systems to better simulate in vivo feedback and response signals between tissues and to minimize the need for testing in animal models. For example, the devices and assemblies of the presently disclosed subject matter can mimic in vivo tissue environments by allowing for initially segregated tissue cultures that can then be linked through fluid flow to measure integrated tissue response. The devices and assemblies of the present disclosure can allow for cell culture integration and media flow activated on demand. The devices and assemblies of the presently disclosed subject matter can provide a pumpless system using surface tension, gravity, and channel geometries. The devices and assemblies of the present disclosure can provide timed and tempered nutrient flow through integrated channels. The devices and assemblies of the present disclosure can provide an option to induce toxin exposure (e.g., drug exposure) at a particular cell site.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

FIG. 1 is a perspective view of a fluidics device 100 in accordance with embodiments of the present disclosure. The fluidics device 100 can include a dosing well 110 positioned upstream from a plurality of wells 120 for containing a respective host fluid, and one or more channels 130 extending between adjacent upstream and downstream wells 120 to define a channel fluid flow path 130 there between such that a dosing fluid 1 deposited into the dosing well 110 flows to the respective host fluid of the adjacent downstream well 120 along the channel fluid flow path 130 there between, and the respective host fluid subsequently flows to each adjacent downstream well 120 along the channel fluid flow path 130 there between.

According to one or more embodiments, the fluidics device 100 can have a structure such that each adjacent downstream well 120 is oriented in a step-down position relative to its adjacent upstream well 120. An example of a fluidics device 100 having this step-down well positioning structure is shown in FIG. 1.

According to one or more embodiments, the fluidics device 100 can include a wick 140 downstream from at least a portion of the plurality of wells 120. The wick 140 is in fluid contact with the channel fluid flow path 130 for regulating fluid flow through the plurality of wells 120. For purposes of the specification and claims, the term "wick" is meant to be used in the broadest sense to refer to a piece of material that can convey liquid by capillary action.

According to one or more embodiments, the fluidics device 100 can include a dosing well channel 150 extending from a bottom of the dosing well 110 to the channel fluid flow path 130 such that the dosing fluid 1 flows to the respective host fluid of the adjacent downstream well 120 through the dosing well channel 150 and along the channel fluid flow path 130. A side of the dosing well 110 can define an angle of greater than 90° extending from a bottom of the dosing well 110 up to the channel fluid flow path 130 of the adjacent well 120. According to one or more embodiments, the fluidics device 100 can include a collection well 170 downstream from the plurality of wells 120 to collect the respective host fluid after having flowed through the plurality of wells 120. The collection well 170 of the fluidics device 100 can include a floor that defines a divot 180, wherein the floor is angled such that the divot 180 is defined at a lower portion of the floor. In certain embodiments according to the present disclosure as described herein below, the lower portion of the floor of the collection well 170 can define an aperture as an alternative to the divot 180. In another example, the divot 180 can be converted to an aperture for use of the fluidics device 100 in an assembly as described herein below.

In accordance with embodiments of the present disclosure, the collection well 170 of fluidics device 100 can include one or more collection well channels 210 extending from the channel fluid flow path 130 to a bottom of the collection well 170 such that the respective host fluid of the adjacent upstream well 120 flows along the channel fluid flow path 130 and through the collection well channel 210 into the collection well 170. The collection well channel 210 can have a width ranging from about 10 to 3500 microns and a depth ranging from about 10 to 3500 microns. The collection well 170 can define a ramp extending from a bottom of the collection well 170 up to the channel fluid flow path 130 of the adjacent upstream well 120. The ramp can include 1, 2, 3, or 4 of the collection well channels 210 that are contiguous with the ramp.

Figure 2:
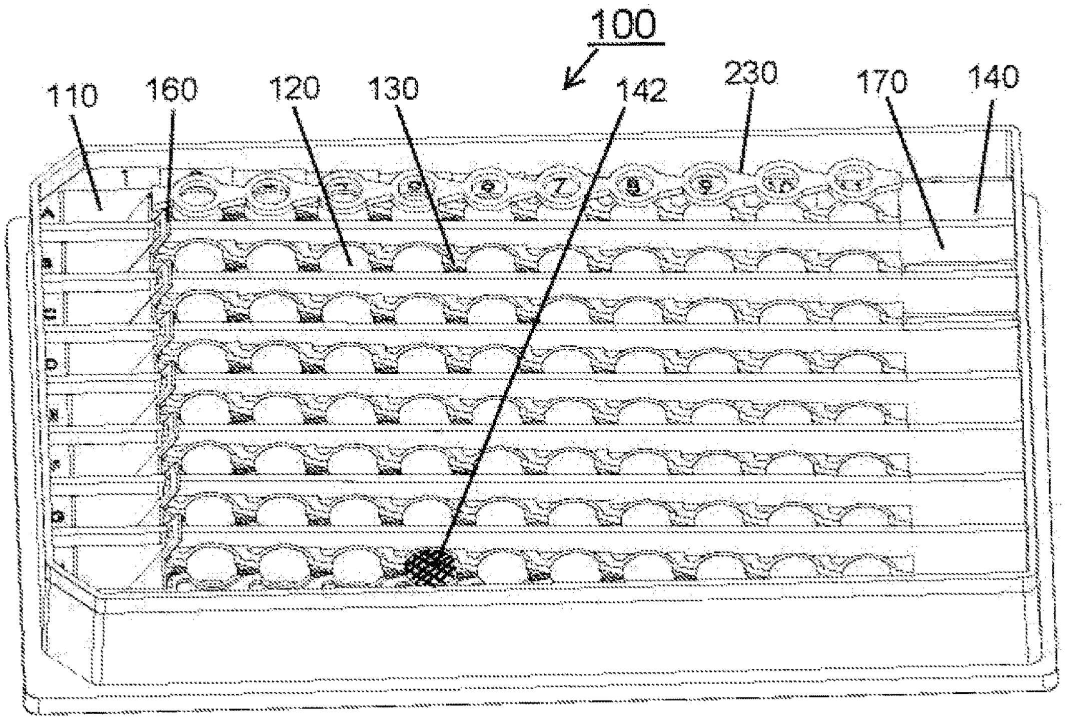
FIG. 2 is a perspective view of the fluidics device of FIG. 1 illustrating dosing well channel cover to enclose dosing well channel and channel cover to enclose the one or more channels extending between the adjacent wells in accordance with embodiments of the present disclosure.

FIG. 2 is a perspective view of the fluidics device 100 in accordance with embodiments of the present disclosure. FIG. 2 illustrates that the fluidics device 100 can include a dosing well channel cover 160 configured to enclose the dosing well channel 150. An example of the dosing well channel cover 160 is shown in FIG. 2 where each of the 8 dosing wells (A-H) are covered with the dosing well channel cover 160. FIG. 2 also illustrates that the fluidics device 100 can include a channel cover 230 configured for engagement on top of the one or more channels 130 extending between the adjacent wells 120 to enclose the channels 130.

The wick of the present disclosure can define any shape that is suitable for being in fluid contact with the channel fluid flow path 130 and for regulating fluid flow through the plurality of wells 120. For example, the wick of the presently disclosed subject matter can be any absorbent material. The wick can regulate fluid flow through the plurality of wells 120 at a rate ranging from 0.0007 ml/min to 30 ml/min. In one example, the respective host fluid after having flowed through each of the plurality of wells 120 and onto the wick can evaporate off the wick.

Figure 3A:
FIGS. 3A-3C illustrate the wick separate from the fluidics device of FIG. 2 in accordance with embodiments of the present disclosure.
Figure 3B:
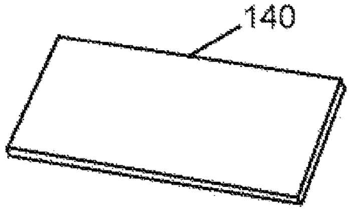
Figure 3C:
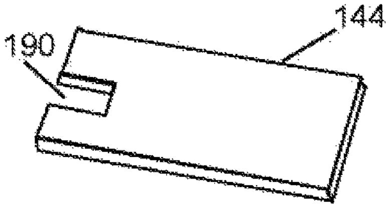

FIG. 2 illustrates two examples of the wick (i.e wick 140 and wick 142) at separate positions downstream from a portion of the plurality of wells 120. FIGS. 3A-3C illustrate the wick in accordance with one or more embodiments of the present disclosure. FIG. 3A illustrates an example of the wick 142 having a cylindrical shape. FIG. 3C illustrates an example of the wick 140 defining a generally flat shape. The wick defining a generally flat shape can define a gap such that only a portion of an edge of the wick is in fluid contact with the channel fluid flow path 130. FIG. 3C illustrates an example of the wick 144 defining a gap 190.

The wick 142 defining a cylindrical shape is illustrated in FIG. 2 and FIG. 3A. The wick of the present disclosure can be positioned anywhere downstream from at least a portion of the plurality of wells 120. For example, the wick 142 defining a cylindrical shape is shown contained in well 120 in row eight of the fluidics device 100 in FIG. 2 such that the wick 142 is in fluid contact with the channel fluid flow path 130 for regulating fluid flow through the plurality of upstream wells 120.

The wick can define a generally flat shape. According to one or more embodiments, the wick 140 or 144 defining a generally flat shape can be contained in the collection well 170 such that the wick 140 or 144 is in fluid contact with the channel fluid flow path 130 for regulating fluid flow through the plurality of wells 120. The wick defining a generally flat shape can be carried by a shoulder defined by the collection well 170 such that the wick does not contact a bottom surface of the collection well 170. An example of the wick 140 defining a generally flat shape and carried by a shoulder defined by the collection well 170 is illustrated in FIG. 2 and in FIG. 3B. The wick defining a generally flat shape can be carried by one or more posts defined by the collection well 170 such that the wick does not contact a bottom surface of the collection well 170. In one embodiment, the wick can define a generally flat shape and can be carried by six of the posts defined by the collection well 170 such that the wick does not contact a bottom surface of the collection well 170.

Figure 4:
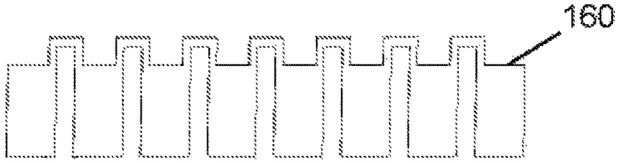
FIG. 4 illustrates the dosing well channel cover separate from the fluidics device of FIG. 2 in accordance with embodiments of the present disclosure.

FIG. 4 illustrates the dosing well channel cover 160 separate from the fluidics device 100.

Figure 5:
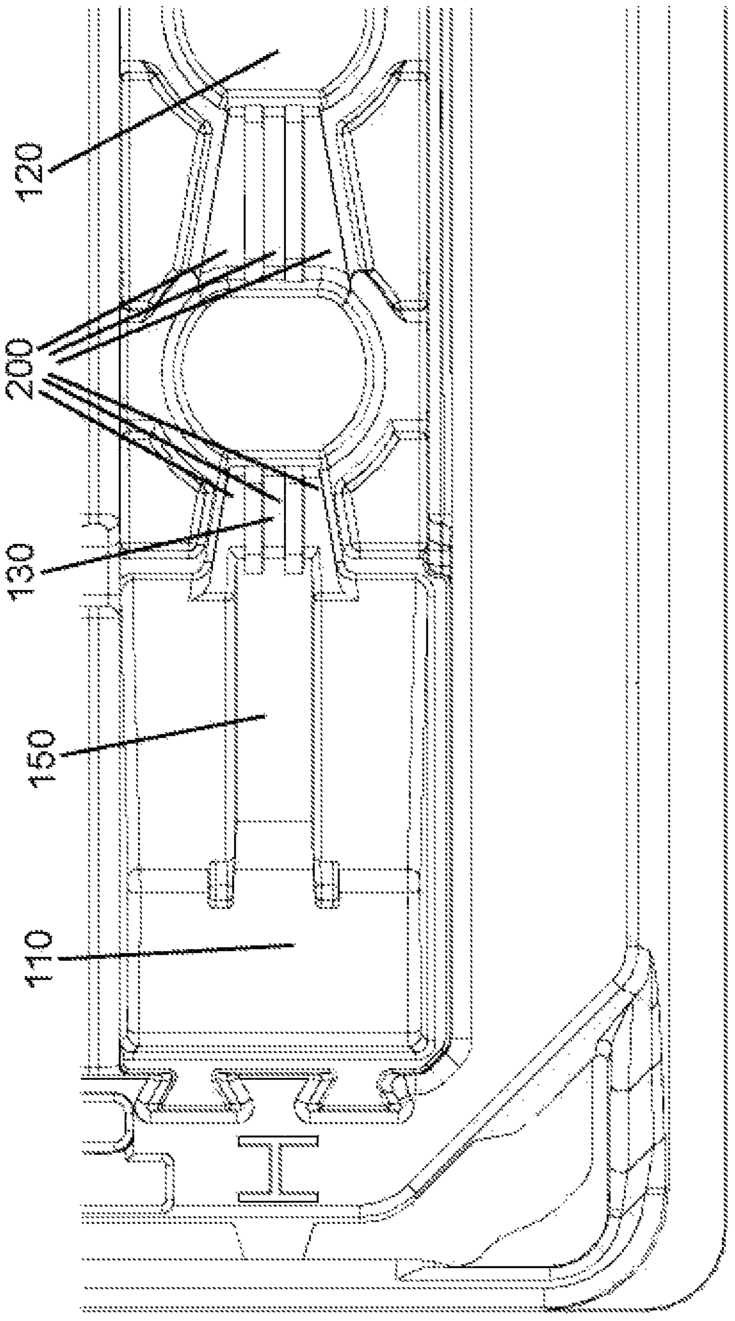
FIG. 5 illustrates an enlarged top view of the fluidics device of FIG. 1 showing an enlarged view of the dosing well, dosing well channel, adjacent downstream well, and the one or more channels extending there between in accordance with embodiments of the present disclosure.

FIG. 5 illustrates a top view of the fluidics device of FIG. 1 showing an enlarged view of the dosing well 110, dosing well channel 150, adjacent downstream well 120, and the one or more channels 130 extending there between in accordance with embodiments of the present disclosure. The dosing well channel 150 can have a width ranging from about 10 to 3500 microns and a depth ranging from about 10 to 3500 microns. The dosing well channel 150 can include 2, 3, or 4 channels contiguous with the dosing well channel 150 and each of the channels can have a width ranging from about 200 to 1500 microns and a depth ranging from about 10 to 1500 microns.

The one or more channels 130 extending between adjacent upstream and downstream wells 120 of the fluidics device 100 can have a width ranging from 10 to 3500 microns and a depth of 10 to 1500 microns. An example of a fluidics device 100 having a single channel 130 is shown in FIG. 5. The channel 130 can define a triangular-shape that extends between each of the adjacent wells 120. The triangular-shape channel 130 can be positioned such that the triangular shape generally converges at each adjacent downstream well 120. An example of a fluidics device 100 having the triangular-shape channel 130 positioned such that the triangular shape generally converges at each adjacent downstream well 120 is shown in FIG. 5.

The fluidics device 100 can have 2, 3, or 4 channels 130 and each of the channels 130 can have a width ranging from 200 to 750 microns and a depth ranging from 10 to 1500 microns. The fluidics device 100 can include 2, 3, or 4 microchannels 200 that are contiguous with the channel 130 and each of the microchannels 200 can have a width ranging from 200 to 750 microns and a depth ranging from 10 to 1500 microns. An example of a fluidics device 100 having 3 microchannels 200 that are contiguous with the triangular-shape channel 130 is shown in FIG. 5.

The channel cover 230 can include 1 or more projections extending from the channel cover 230 such that when the channel cover 230 is engaged on top of the channels 130 of the fluidics device 100 the channel cover 230 defines 2 or more microchannels 200 contiguous with the channel 130. For example, the channel cover 230 can have two projections such that when the channel cover 230 is engaged on top of the channel 130 of the fluidics device 100 the channel cover 230 defines 3 microchannels 200 contiguous with the channel 130. In one embodiment, each of the microchannels 200 defined by the channel cover 230 can have a width ranging from 200 to 750 microns and a depth ranging from 10 to 1500 microns.

The bottom surface of each of the channels 130, the dosing well channel 150, the microchannels 200, and the collection well channels 210 can define different shapes. For example, the channels 130, the dosing well channel 150, the microchannels 200, and the collection well channels 210 can define an arcuate bottom surface or a generally flat bottom surface.

Figure 8:
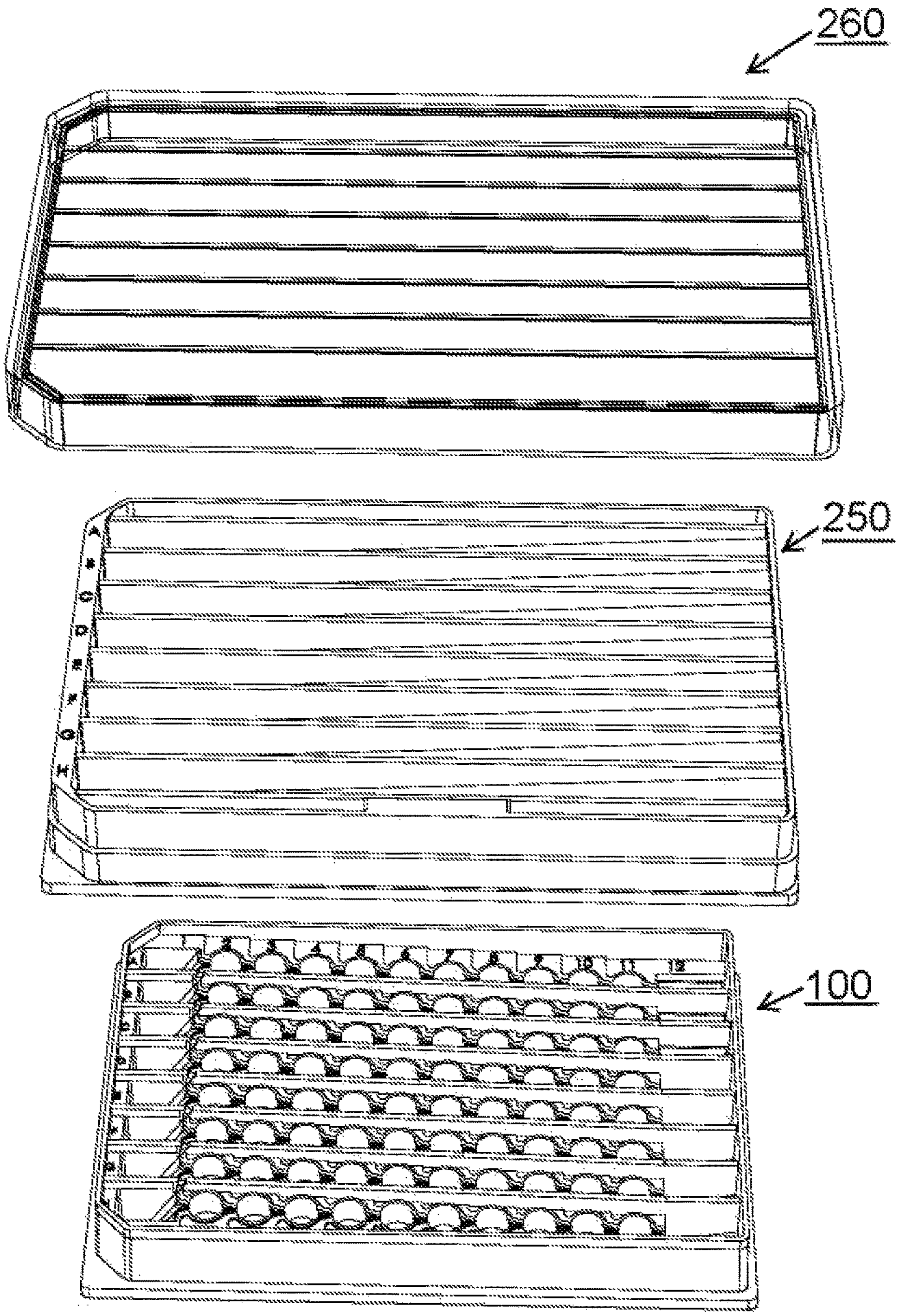
FIG. 8 shows an exploded perspective view of the fluidics device of FIG. 1 as part of an assembly including a reservoir tray nestably engaged on top of the fluidics device and a cover tray nestably engaged on top of the reservoir tray in accordance with embodiments of the present disclosure.

According to one or more embodiments, the fluidics device 100 can have a structure where the plurality of wells 120 are aligned in a row. The fluidics device 100 can have 12 wells in a respective row and a total of 8 rows. An example of a fluidics device 100 having this structure is shown in FIGS. 1, 2, and 8. The fluidics device 100 can have 3 wells in a row and a total of 2 rows. The fluidics device 100 can have 6 wells in a row and a total of 4 rows. The fluidics device 100 can have 8 wells in a row and a total of 6 rows. The fluidics device 100 can have 12 wells in a row and a total of 8 rows. The fluidics device 100 can have 24 wells in a row and a total of 16 rows. The fluidics device 100 can have 48 wells in a row and a total of 32 rows.

According to one or more embodiments, the fluidics device 100 can have a structure where the plurality of wells 120 for containing a respective host fluid are oriented in a configuration such that each downstream well 120 is positioned lower relative to each adjacent upstream well 120 and the dosing well 110 is upstream from the plurality of wells 120 and in fluid communication therewith.

The fluidics device 100 of the presently disclosed subject matter can be employed for any use requiring the tempered flow of fluid between a plurality of wells. According to one or more embodiments, a method for employing the fluidics device 100 includes adding a dosing fluid 1 to the dosing well 110 and adding the respective host fluid to the plurality of wells 120 such that the fluid is in fluid contact with the channel fluid flow path 130, whereby the dosing fluid 1 flows to each of the respective host fluids in the plurality of wells 120 in a tempered manner. The method can include removing an aliquot of the respective host fluid from the wells 120 at one or more time periods to measure the effect of the dosing fluid 1 being tempered through the plurality of wells 120 over time.

The dosing fluid 1 can include, for example, but is not limited to a drug, a legal or illegal drug, a toxin, an agent of warfare, a fragrance, a food spice, an oil, a gas, a metabolite, a compound, a hormone, a solution, a solute, a composite, a nutrient media, differentiation media, or a growth media, and combinations thereof. The plurality of wells 120 can contain a respective cell culture whereby an effect of the tempered exposure to the dosing fluid 1 on the cells can be measured. The effect of the tempered exposure to the dosing fluid 1 on the cell cultures to be measured can be one or more of pharmacokinetics, drug metabolism, toxicity, pre-clinical pharmaceutical studies, cell response, cell receptor response, cell feedback signals, cell growth, cell death, cell differentiation, or cell regeneration, and combinations thereof. The respective cell culture can be, for example, a stem cell culture or a progenitor cell culture.

According to one or more embodiments, the plurality of wells 120 of the fluidics device 100 can contain a respective cell culture, and a method for employing the fluidics device 100 containing the respective cell cultures includes adding a dosing fluid 1 to the dosing well 110, adding the desired respective host fluid to the wells 120 such that the fluid is in fluid contact with the channel fluid flow path 130. Subsequently, the dosing fluid 1 flows to each of the respective host fluids in the plurality of wells 120 in a tempered manner. The method can further include removing an aliquot of the respective host fluid from the wells 120 at one or more time periods to measure the effect of the dosing fluid 1 on the cells.

The fluidics device 100 can be made of any material that is suitable for use in fluid transfer between the plurality of wells 120. The type of material chosen can depend on the desired use of the fluidics device 100. For example, the user of the fluidics device 100 can choose the material based on the dosing well fluid that will be used and the expected interaction of the dosing well fluid with the material. Thus, the fluidics device 100 can be made of any suitable material including, for example, a polymer, a synthetic polymer, a TOPAS® COC polymer, a biodegradable polymer, a plastic, a biodegradable plastic, a thermoplastic, a polystyrene, a polyethylene, a polypropylene, a polyvinyl chloride, a polytetrafluoroethylene, a silicone, a glass, a PYREX, or a borosilicate, or combinations thereof. In addition, the dosing well channel cover 160, the channel cover 230, and the wick 140, 142, 144 may each be made from the same materials as the fluidics device 100. In one example, a user may wish to have each of the fluidics device 100, the dosing well channel cover 160, the channel cover 230, and the wick 140, 142, 144 made from the same material such that the interaction of the dosing well fluid with the material does not vary.

According to one or more embodiments, the surface of one or more of the plurality of wells 120 of the fluidics device 100 can be modified with one or both of a chemical layer or a protein layer to support a cell culture. The protein layer for supporting the cell cultures can include one or more of collagen I, collagen II, collagen III, laminin, or fibronection, or combinations thereof.

Figure 6:
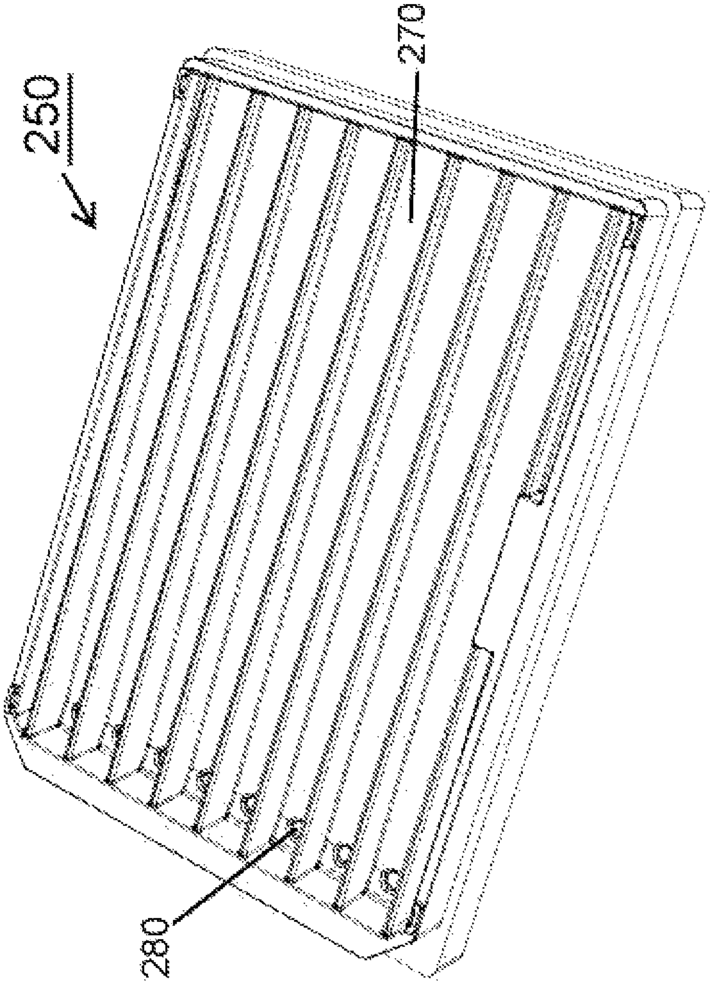
FIG. 6 shows a perspective view of the reservoir tray in accordance with embodiments of the present disclosure
Figure 7:
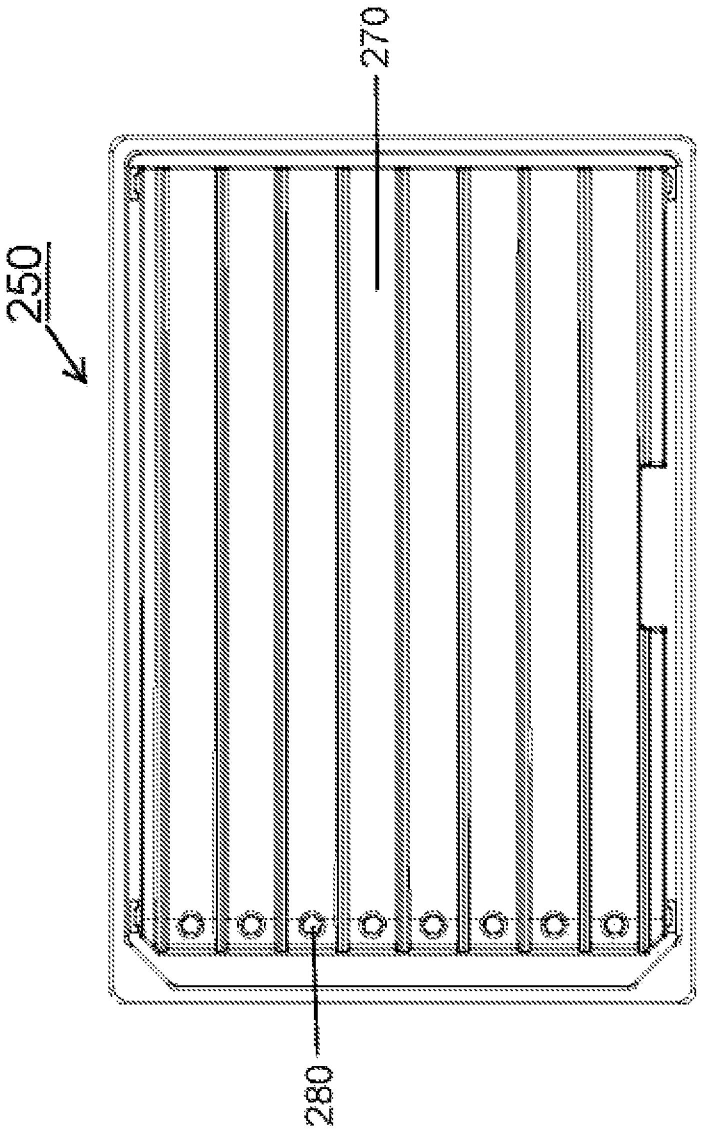
FIG. 7 shows a bottom view of the reservoir tray in accordance with embodiments of the present disclosure.

According to one or more embodiments of the presently disclosed subject matter, an assembly is provided for allowing fluid flow between the plurality of wells 120 of the fluidics device 100. The assembly can include the fluidics device 100 and a reservoir tray 250 configured for nesting engagement on top of the fluidics device 100. FIG. 6 shows a perspective view of the reservoir tray in accordance with embodiments of the present disclosure. FIG. 7 shows a bottom view of the reservoir tray in accordance with embodiments of the present disclosure. According to one or more embodiments, an assembly is provided that includes the fluidics device 100, the reservoir tray 250, and a cover tray 260 configured for nesting engagement on top of the reservoir tray 250 or the fluidics device 100. FIG. 8 shows an exploded perspective view of the fluidics device 100 as part of an assembly including the reservoir tray nestably engaged on top of the fluidics device 100 and the cover tray 260 nestably engaged on top of the reservoir tray in accordance with embodiments of the present disclosure.

According to one or more embodiments of the presently disclosed subject matter, an assembly is provided for allowing fluid flow between the plurality of wells 120 of the fluidics device 100, the assembly including the fluidics device 100 and the reservoir tray 250 configured for nesting engagement on top of the fluidics device 100. Turning to FIGS. 6 and 7, the reservoir tray 250 can include at least one chamber 270 for containing a respective chamber fluid and an aperture 280 defined in the chamber floor and configured such that the aperture 280 is positioned above the dosing well 110 of the fluidics device 100 when in nesting engagement with the fluidics device 100. The floor of the chamber 270 can be angled and the aperture 280 can be defined at a lower portion of the chamber floor such that the chamber fluid flows through the aperture 280 into the dosing well 110 when the reservoir tray 250 and the fluidics device 100 are nestably engaged. When nestably engaged, the reservoir tray 250 can be positioned just above the fluidics device 100 and the respective chamber fluid flows from each chamber 270 of the reservoir tray 250 through each aperture 280 and into each dosing well 110 of the fluidics device 100.

According to one or more embodiments, the assembly can further include the cover tray 260 configured for nesting engagement on top of the reservoir tray 250 of the fluidics device 100. According to one or more embodiments, the assembly can include one or more additional reservoir trays 250 configured for nesting engagement on top of the fluidics device 100.

Figure 9:
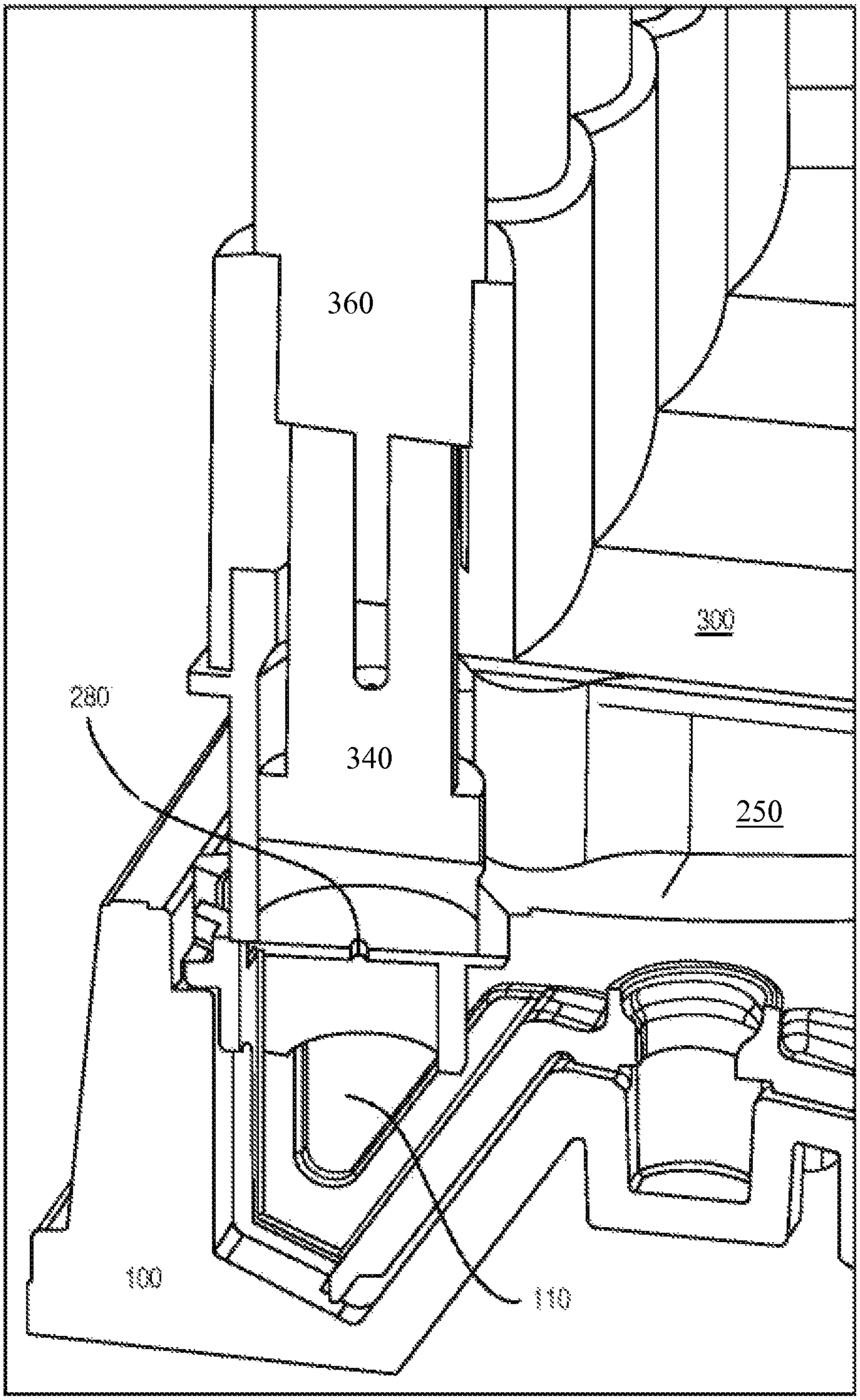
FIG. 9 shows a cross-section view of the piston assembly engaged on top of the fluidics device in accordance with one or more embodiments of the present disclosure.
Figure 10:
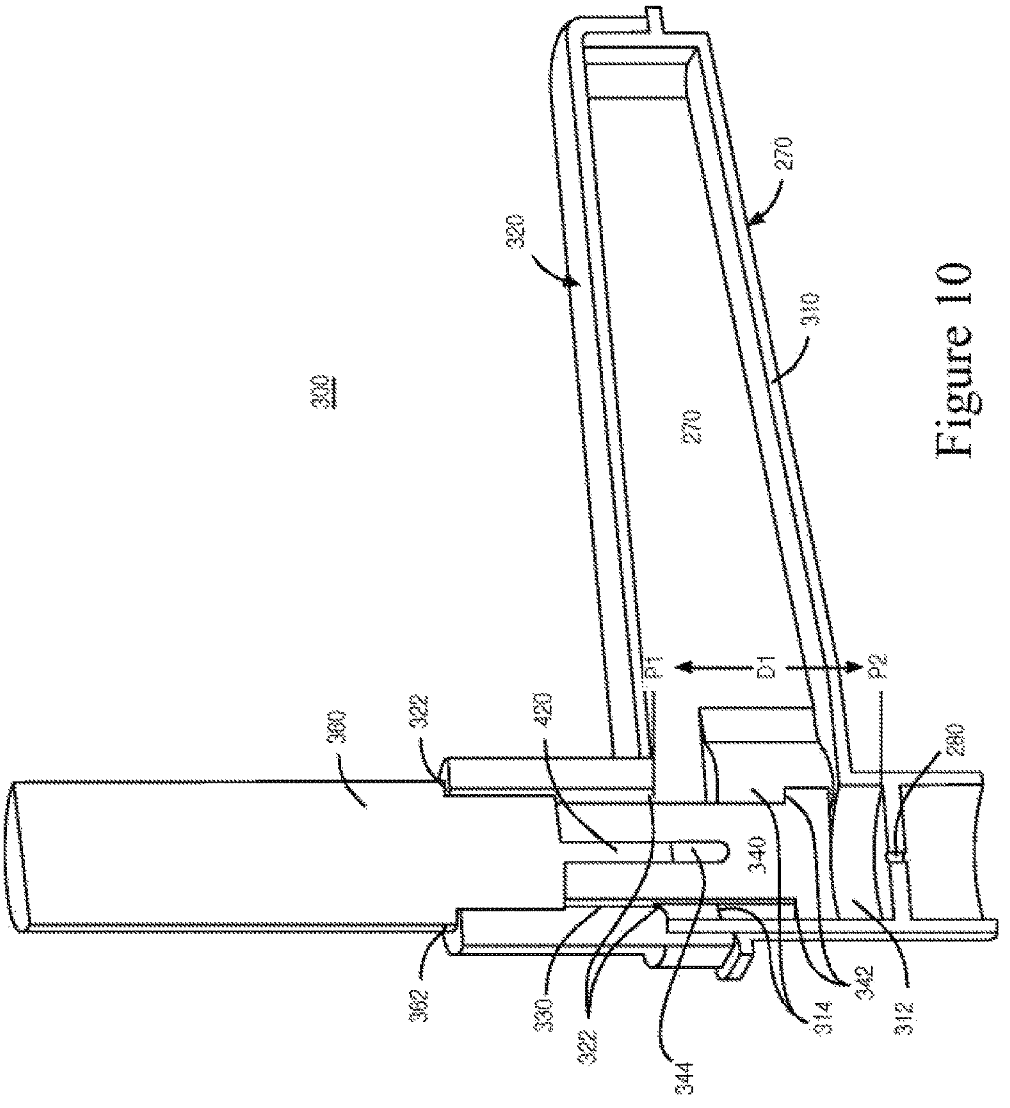
FIG. 10 shows a cross-section view of the piston assembly in accordance with one or more embodiments of the present disclosure.
Figure 11:
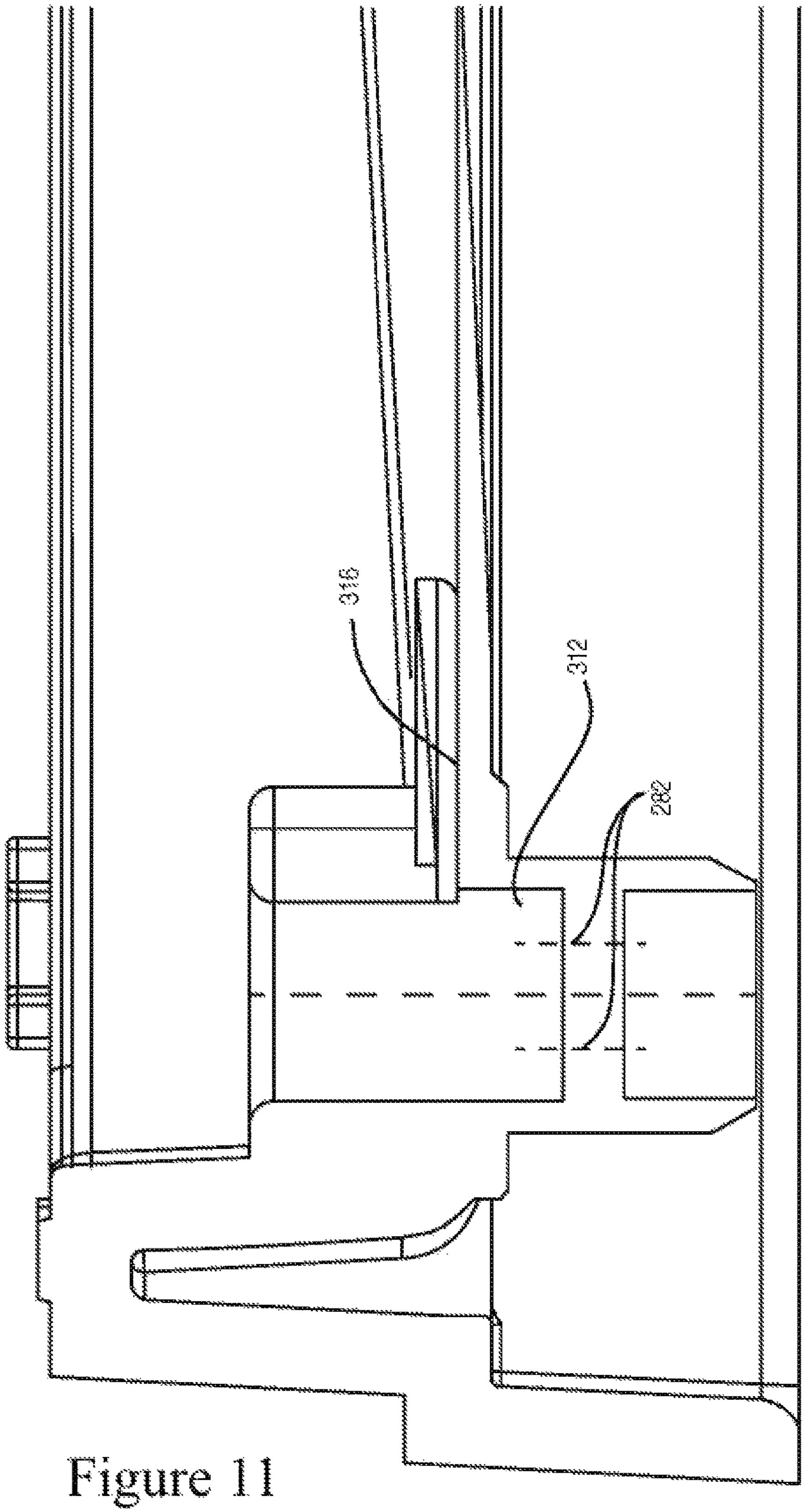
FIG. 11 shows a side view of the piston assembly in accordance with one or more embodiments of the present disclosure.
Figure 12:
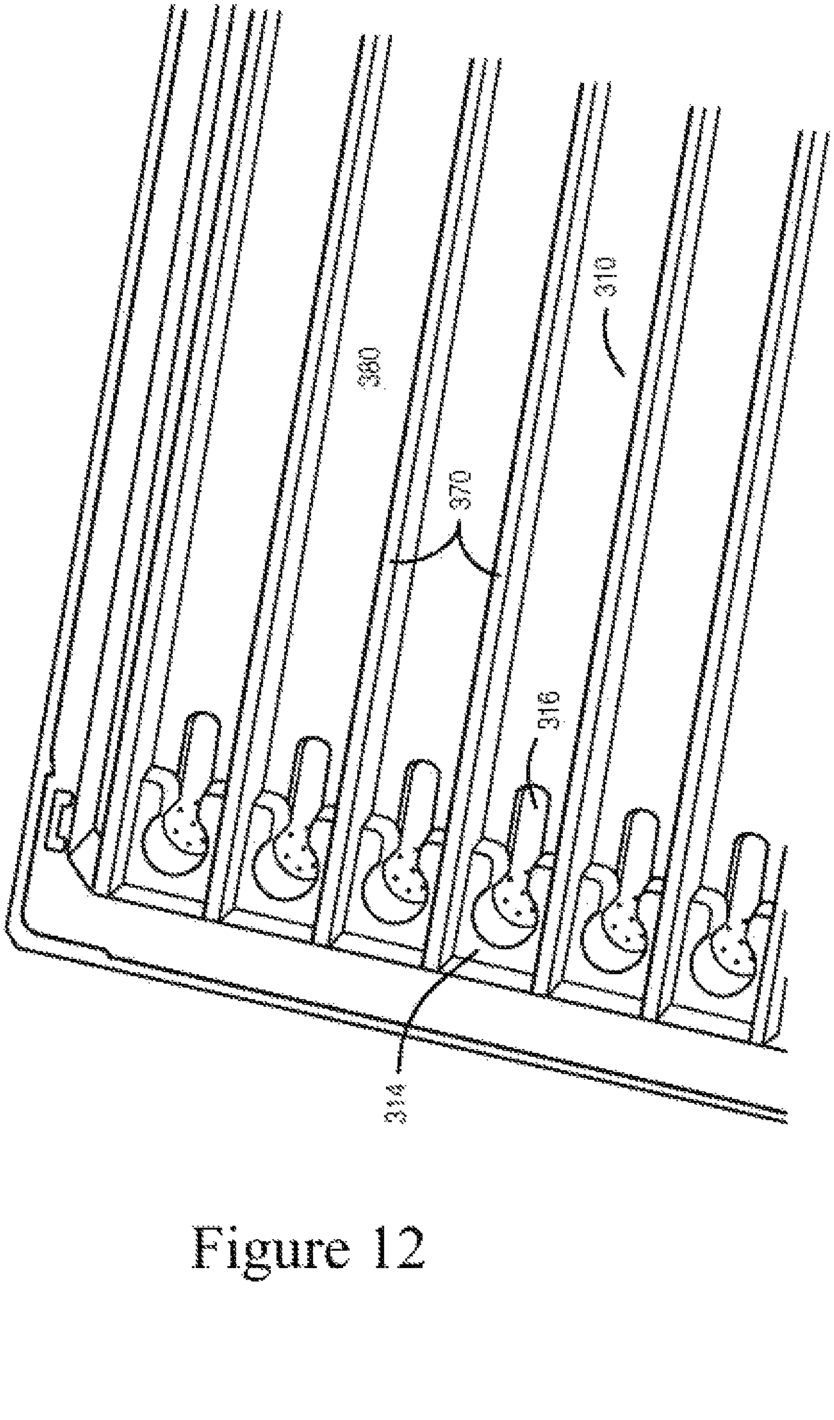
FIG. 12 shows a top view of the reservoir tray of the piston assembly in accordance with one or more embodiments of the present disclosure.
Figure 13:
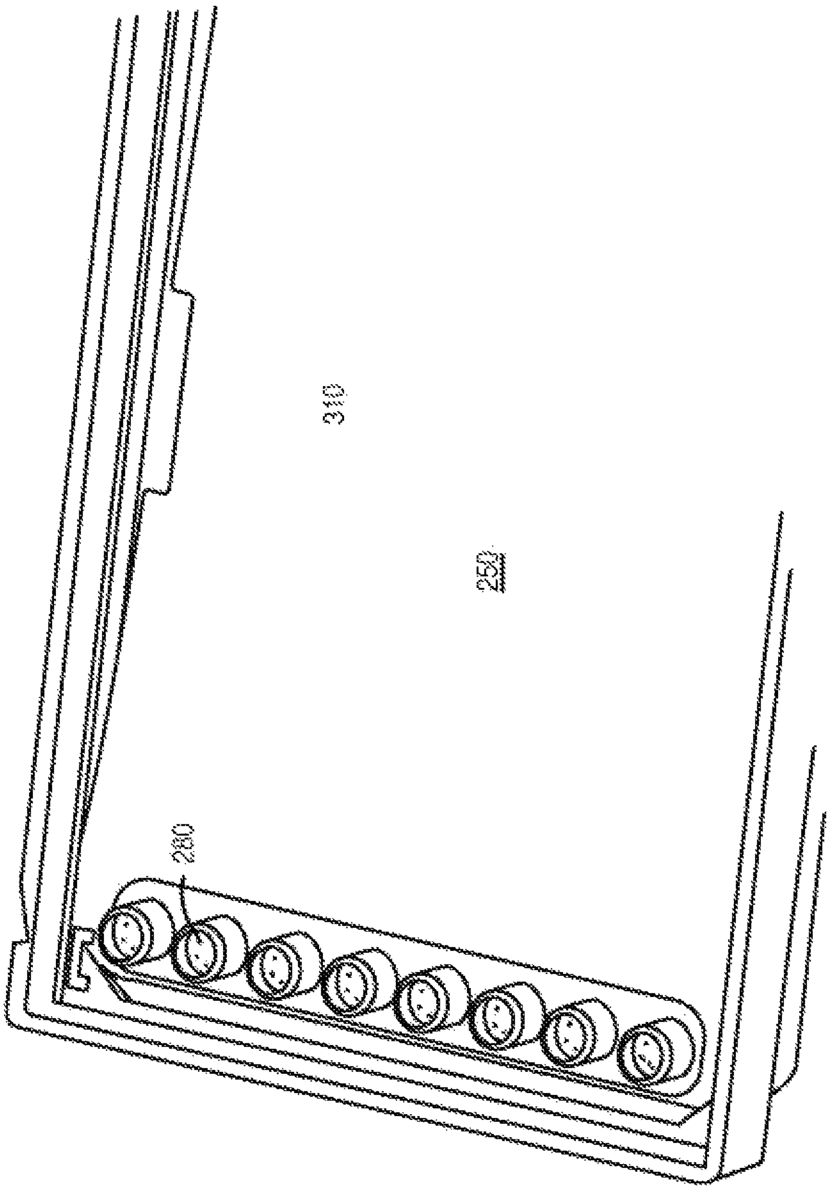
FIG. 13 shows a bottom view of the reservoir tray of the piston assembly in accordance with one or more embodiments of the present disclosure.

According to one or more embodiments of the presently disclosed subject matter, a piston assembly 300 is provided for allowing fluid flow between a reservoir tray 250 and a fluidics device 100, the piston assembly 300 including the reservoir tray 250 configured for nesting engagement with the fluidics device 100. FIG. 9 shows a cross-section view of the piston assembly 300 engaged on top of the fluidics device 100 in accordance with one or more embodiments of the present disclosure. FIG. 10 shows a cross-section view of the piston assembly 300 in accordance with one or more embodiments of the present disclosure. FIG. 11 shows a side view of the piston assembly 300 in accordance with one or more embodiments of the present disclosure. FIG. 12 shows a top view of the reservoir tray 250 of the piston assembly 300 in accordance with one or more embodiments of the present disclosure. FIG. 13 shows a bottom view of the reservoir tray 250 of the piston assembly 300 in accordance with one or more embodiments of the present disclosure.

Turning to FIGS. 9-11, the reservoir tray 250 can include a liquid chamber 270 defining a chamber floor 310 for containing a dosing fluid 1, an aperture 280 defined in the chamber floor 310 and positioned above a dosing well 110 of the fluidics device 100 when the reservoir tray 250 is nestably engaged with the fluidics device 100. The chamber floor 310 can be angled and the aperture 280 can be defined at a lower portion of the chamber floor 310 such that the dosing fluid 1 flows through the aperture 280 into the dosing well 110 of the fluidics device 100 when the reservoir tray 250 and the fluidics device 100 are nestably engaged. The piston assembly 300 can further includes a reservoir cover 320 defining a piston chamber 330 that receives at least a portion of a piston 340 for allowing the piston 340 to translate between a first position P1 a distance D1 from the aperture 280 and a second position P2 proximal to the aperture 280. Additionally, the piston assembly 300 can include a crank 360 engaged with the piston 340 for translating the piston 340 between the first position P1 and the second position P2 such that the translation from the first position P1 to the second position P2 results in a portion of the dosing fluid 1 flowing through the aperture 280 to the dosing well 110 when the reservoir tray 250 and the fluidics device 100 are nestably engaged.

Alternatively, in accordance with one or more embodiments of the presently disclosed subject matter, a piston assembly 300 is provided for allowing fluid flow between a reservoir tray 250 and a fluidics device 100, the piston assembly 300 including a reservoir tray 250 configured for nesting engagement with a fluidics device 100 and including a liquid chamber 270 defining a chamber floor 310 and dividing walls 370 creating subchambers 380 for housing a dosing fluid 1. Each of the subchambers 380 can include an aperture 280 defined in the chamber floor 310 and positioned above a dosing well 110 of the fluidics device 100 when the reservoir tray 250 is nestably engaged with the fluidics device 100. The chamber floor 310 can be angled and the aperture 280 can be defined at a lower portion of the chamber floor 310 such that the dosing fluid 1 flows through the aperture 280 into the dosing well 110 of the fluidics device 100 when the reservoir tray 250 and the fluidics device 100 are nestably engaged. The reservoir cover 320 can define a piston chamber 330 housing a piston 340 for each of subchambers 380 for allowing the piston 340 to translate a between a first position P1 a distance D1 from the aperture 280 and a second position P2 proximal to the aperture 280. Additionally the piston assembly 300 can include a crank assembly 390 engaged with the pistons 340 for translating the pistons 340 such that a portion of the dosing fluid 1 flows through the aperture 280 when the reservoir tray 250 and the fluidics device 100 are nestably engaged.

The piston chamber 330 serves at least two purposes. First, the piston chamber 330 serves to guide and locate the pistons 340 during translation between the first position P1 and the second position P2. In one example, the piston chamber 330 may have a 5.2 mm diameter and the piston 340 may have a 5.0 mm diameter such that the pistons 340 do not bind to the piston chamber. Secondly, the piston chamber 330 serves, along with the reservoir cover 320 generally, to form a barrier between the sterile and non-sterile components, namely the crank 360, crank assembly 390, solenoid 400 and/or electronics unit 440.

According to one or more embodiments, the piston(s) 340 translates from the first position P1 to the second position P2 a distance D1 such that a volume of dosing fluid 1 is transferred from the liquid chamber 270 of the reservoir tray 250 to the dosing well 110 of the fluidics device 100 through the aperture 280. In some embodiments, the piston(s) 340 repeatedly translates between the first position P1 and second position P2 a distance D1 such that the same volume of dosing fluid 1 is repeatedly transferred from the liquid chamber 270 of the reservoir tray 250 to the dosing well 110 of the fluidics device 100. In alternative embodiments, the piston(s) 340 may translate varying distances D1 during each translation, each distance D1 having a different starting first position P1 and therefore transferring a different volume of dosing liquid upon each translation. In one example, the piston(s) may translate at certain predetermined time intervals. Any number of translations of the piston(s) 340 may occur at any number of time intervals, whether varying or the same, and each of these translations may occur over a distance D1, which may vary or remain the same.

According to one or more embodiments, a piston assembly 300 can include an aperture 280 defining one or more openings 282. The one or more openings 282 can be configured for communication with the dosing fluid 1 in the liquid chamber 270 such that surface tension of the dosing fluid 1 maintains the dosing fluid 1 in the liquid chamber 270 until the piston 340 is translated from the first position P1 to the second position P2.

According to one or more embodiments, a piston assembly 300 can include a piston chamber 330 defining a chamber lip 332 for engaging with a piston catch 342 defined by a piston 340, thereby retarding the translation of the piston 340 when the piston 340 translates from the second position P2 to the first position P1.

According to one or more embodiments, a piston assembly 300 can include a reservoir cover 320 defining a cover lip 322 for engaging with a crank catch 362 defined by the crank 360, thereby retarding the translation of the crank 360 when the piston 340 is translating from the second position P2 to the first position P1.

According to one or more embodiments, a piston assembly 300 can include a chamber floor 310 defining a piston well 312 including the aperture 280 for receiving the piston 340 in the second position P2 and the dosing fluid 1.

According to one or more embodiments, a piston assembly 300 can include a piston well 312 having a piston well wall 314 for nestably engaging at least half of the circumference of the piston 340 during the entire translation between the first position P1 and the second position P2 and for delivering the dosing fluid 1 to the piston well 312.

Additionally, the piston well wall 314 can aid in preventing the dosing liquid 1 from collecting between the piston 340 and the wall of the subchamber 380 at the lower portion of the liquid chamber 270.

According to one or more embodiments, a piston assembly 300 can include a chamber floor 310 defining a floor recess 316 at the lower portion of the chamber floor 310 proximal to the piston well 312 and the piston well wall 314 for receiving the dosing fluid 1 and delivering the dosing fluid 1 to the piston well 312.

According to one or more embodiments, a piston assembly 300 can include a crank 360 having a pin 420 engaged within a piston channel 344 defined in the piston 340 for engaging the crank 360 to the piston 340. Further, a piston assembly 300 can include a crank 360 in communication with a solenoid 400.

Figure 14:
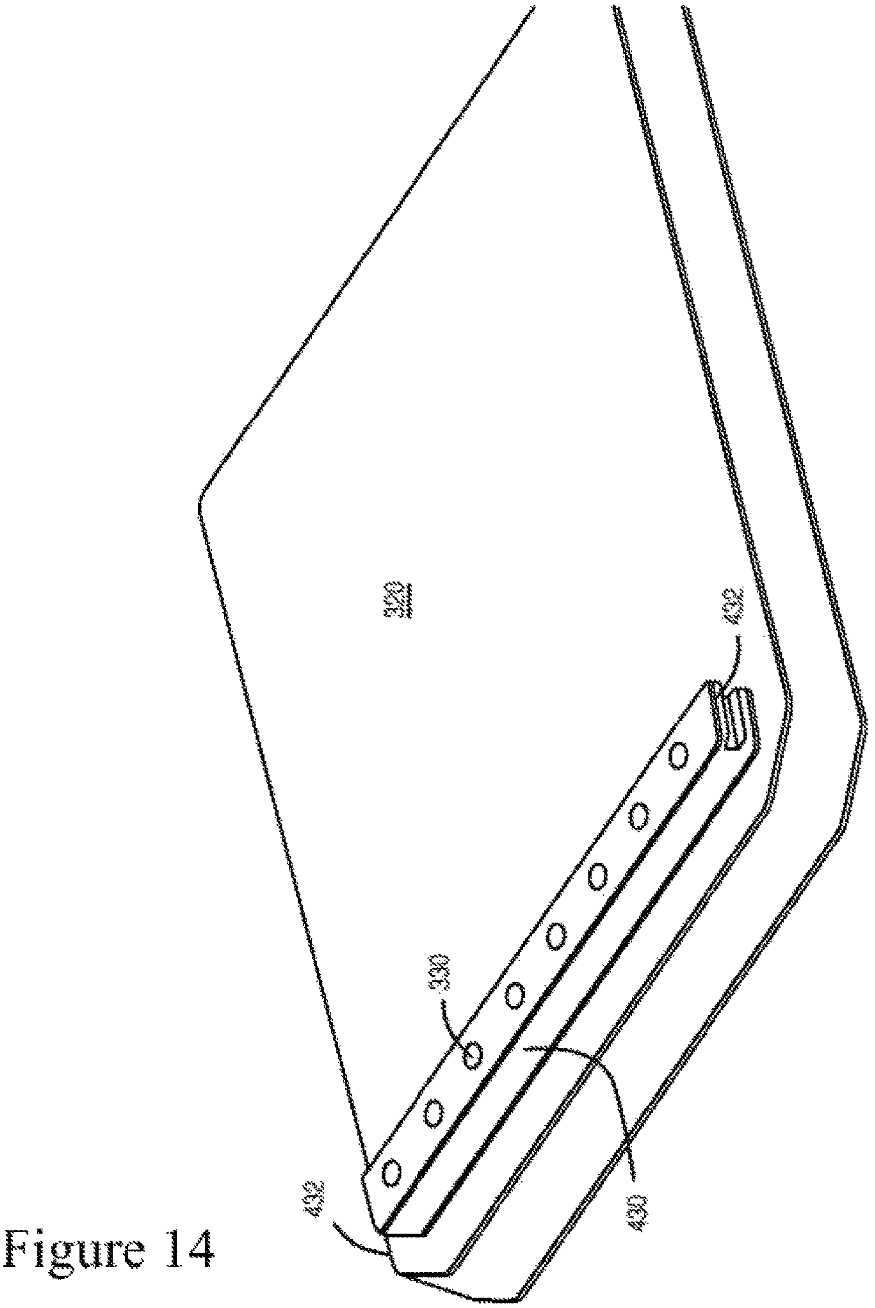
FIG. 14 shows a top view of the reservoir cover of the piston assembly in accordance with one or more embodiments of the present disclosure.

FIG. 14 shows a top view of the reservoir cover 320 of the piston assembly 300 in accordance with one or more embodiments of the present disclosure. In FIG. 14, the reservoir cover 320 defines several piston chambers 330, each housing a piston 340 corresponding to each underlying subchamber 380 and allowing each piston 340 to translate a between a first position P1 and a second position P2. The piston chambers 330 can define a piston guide 430 extending above the remainder of the reservoir cover 320 for guiding the translation of the pistons 340 between the first position and the second position. Further, the piston guide 430 defines electronic guides 432 on each end for receiving an electronic unit 440 (not shown) for controlling the translation of the pistons 340, cranks 360 and/or crank assembly 390. In one example, the electronics unit 440 may include a timer that can be programmed via a dip switch so that varying piston 340 translation cycles may be implemented.

Figure 15:
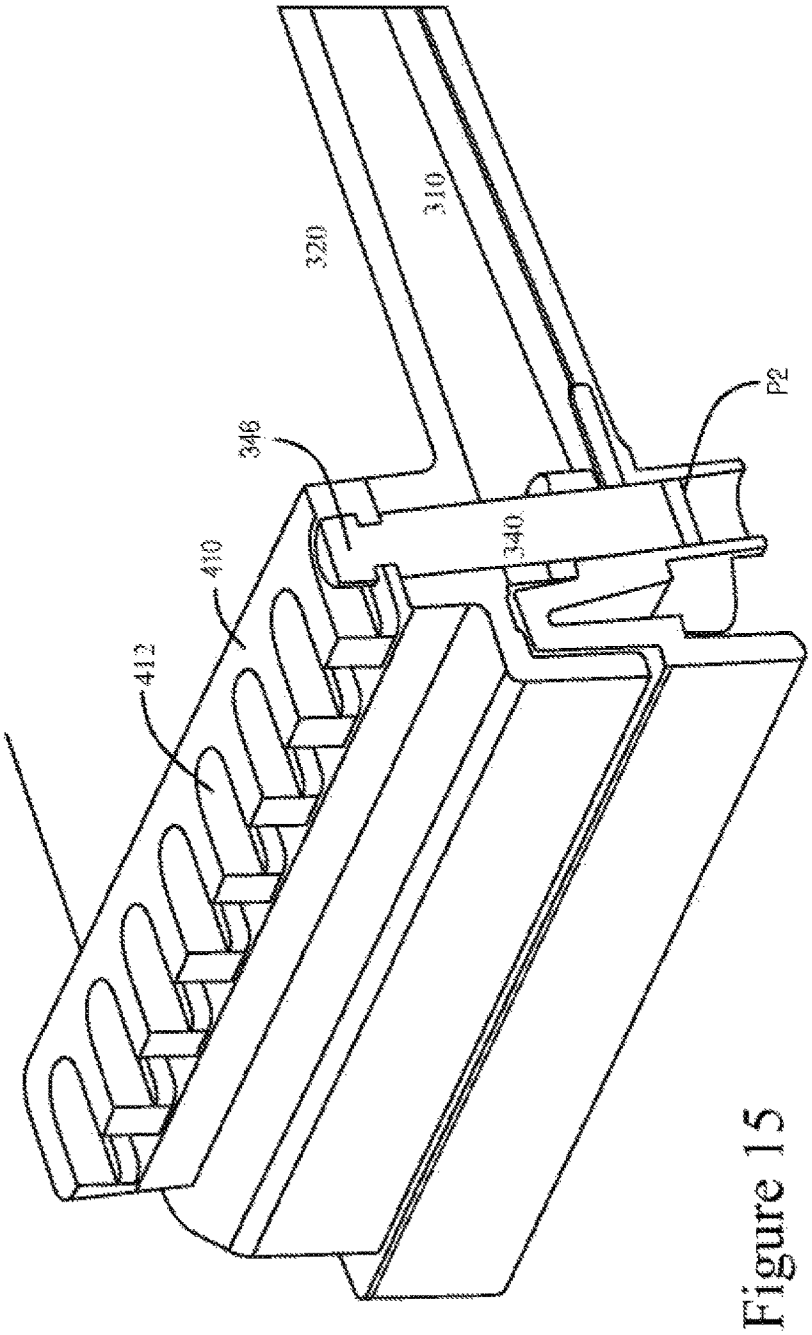
FIG. 15 illustrates the piston assembly including a piston bar in accordance with one or more embodiments of the present disclosure.

FIG. 15 illustrates the piston assembly 300 including a piston bar 410 in accordance with one or more embodiments of the present disclosure. A piston assembly 300 can include a crank assembly 390 having one or more cranks 360. Each crank 360 can be engaged with the piston 340 of each of one of the subchambers 380 for translating the piston 340 between the first position P1 and the second position P2. In some embodiments, each crank 360 can be in communication with a solenoid 400 including a pin 420 engaged with a piston channel 344 defined by each piston 340.

According to one or more embodiments, a piston assembly 300 can include pistons 340, each of the pistons 340 defining a piston head 346. Further, the piston assembly can include a crank assembly 390 having a piston bar 410 engaged with all of the piston heads 346 for translating the pistons 340 simultaneously between the first position P1 and the second position P2. The crank assembly can additionally include at least one crank 360 engaged with the piston bar 410 for translating the piston bar 410, thereby translating the pistons 340 between the first position P1 and the second position P2. The at least one crank 360 can be in communication with at least one solenoid 400 including a pin 420 engaged with a piston bar channel 412 defined by the piston bar 410. In one example, three 13.5 mm solenoids 400 can be in communication with a crank assembly 390. In another example, one 20 mm solenoid 400 can be in communication with a piston bar 410. In an alternative embodiments an electronics unit 440 can be in communication with one or more solenoids 400 for translating the piston bar 410, crank assembly 390, cranks 360 and/or pistons 340.

The piston assembly 300 can be made of any material that is suitable for allowing fluid flow between a reservoir tray 250 and a fluidics device 100. The type of material chosen can depend on the desired use of the piston assembly 300. For example, the user of the piston assembly 300 can choose the material based on the dosing fluid 1 that will be used and the expected interaction of the dosing fluid 1 with the material. Thus, the piston assembly 300 can be made of any suitable material including, for example, a polymer, a synthetic polymer, a TOPAS® COC polymer, a biodegradable polymer, a plastic, a biodegradable plastic, a thermoplastic, a polystyrene, a polyethylene, a polypropylene, a polyvinyl chloride, a polytetrafluoroethylene, a silicone, a glass, a PYREX, or a borosilicate, or combinations thereof. In addition, the fluidics device 100, the dosing well channel cover 160, the channel cover 230, and the wick 140, 142, 144 may each be made from the same materials as the piston assembly 300. In one example, a user may wish to have each of the piston assembly 300, the fluidics device 100, the dosing well channel cover 160, the channel cover 230, and the wick 140, 142, 144 made from the same material such that the interaction of the dosing well fluid with the material does not vary.

Figure 16:
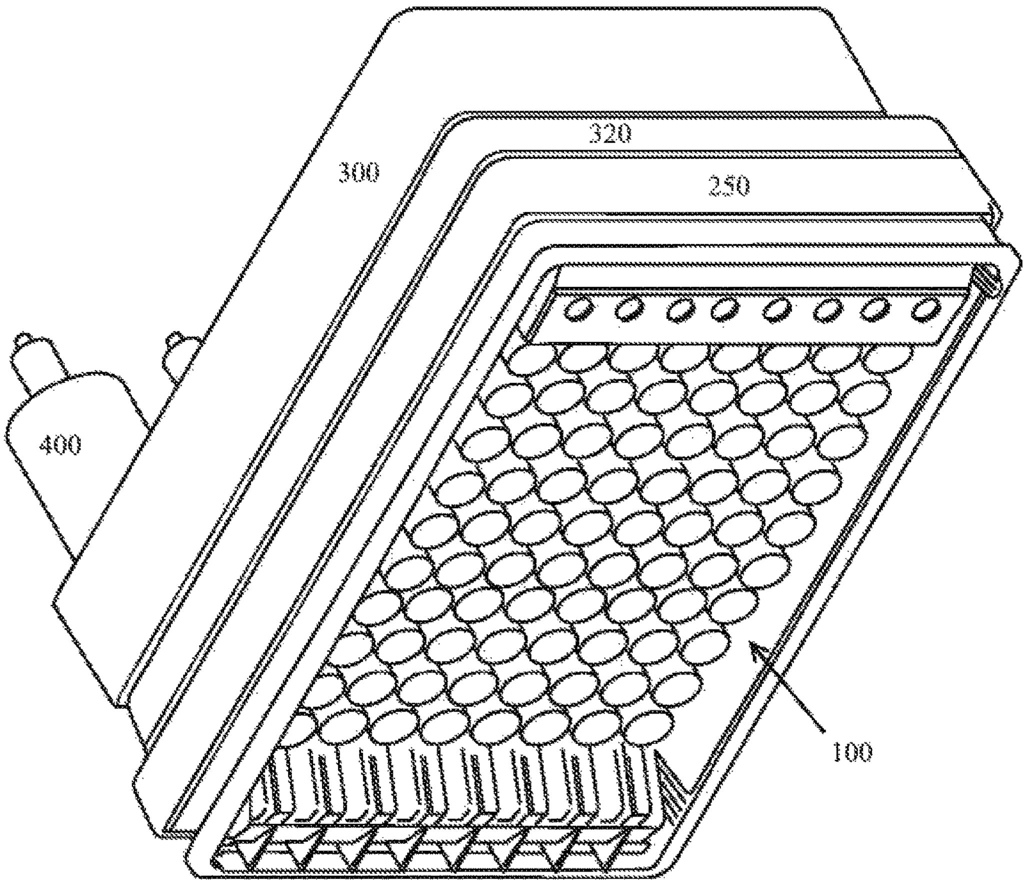
FIG. 16 shows a bottom perspective view of the piston assembly engaged on top of the fluidics device in accordance with one or more embodiments of the present disclosure.
Figure 17:
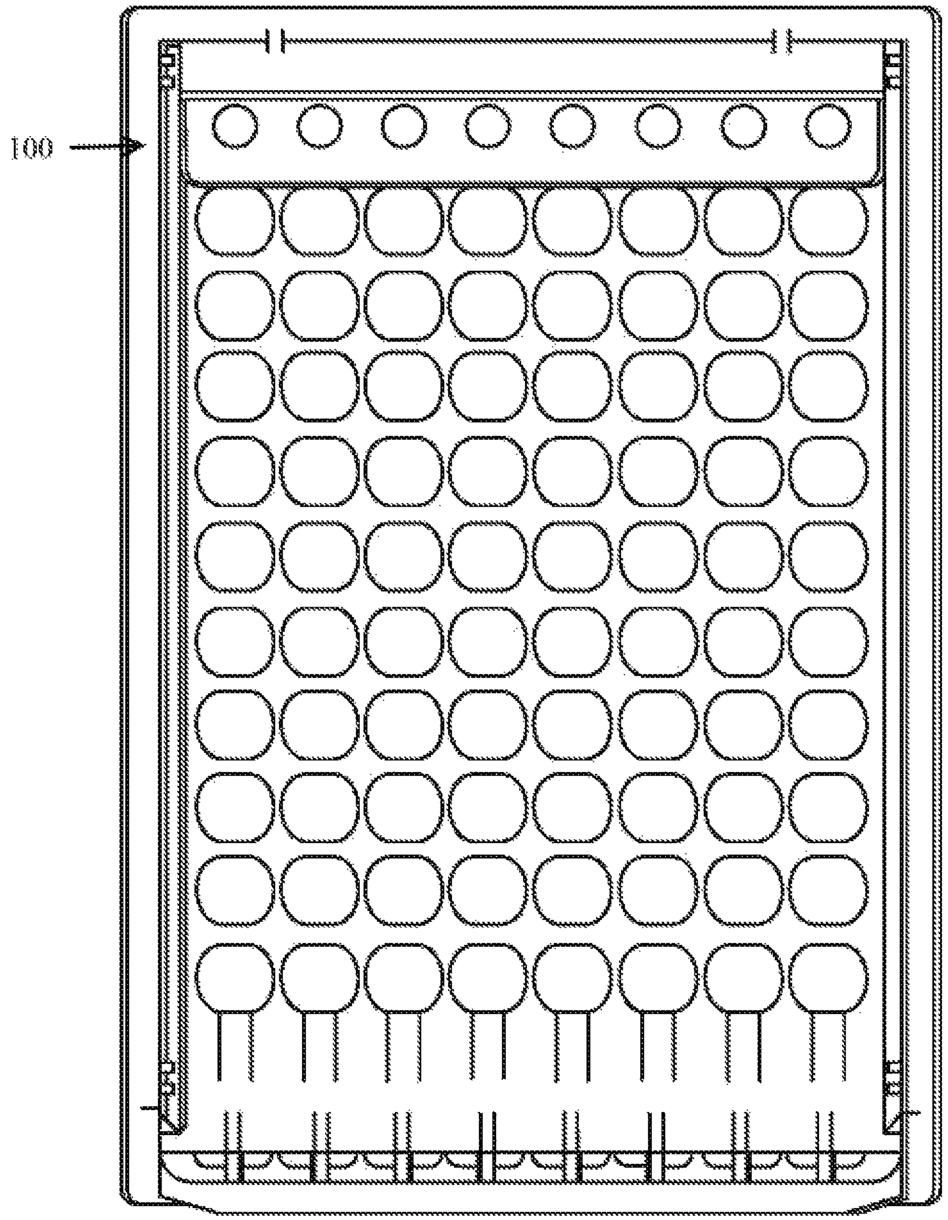
FIG. 17 shows a bottom view of the fluidics device in accordance with one or more embodiments of the present disclosure.
Figure 18:
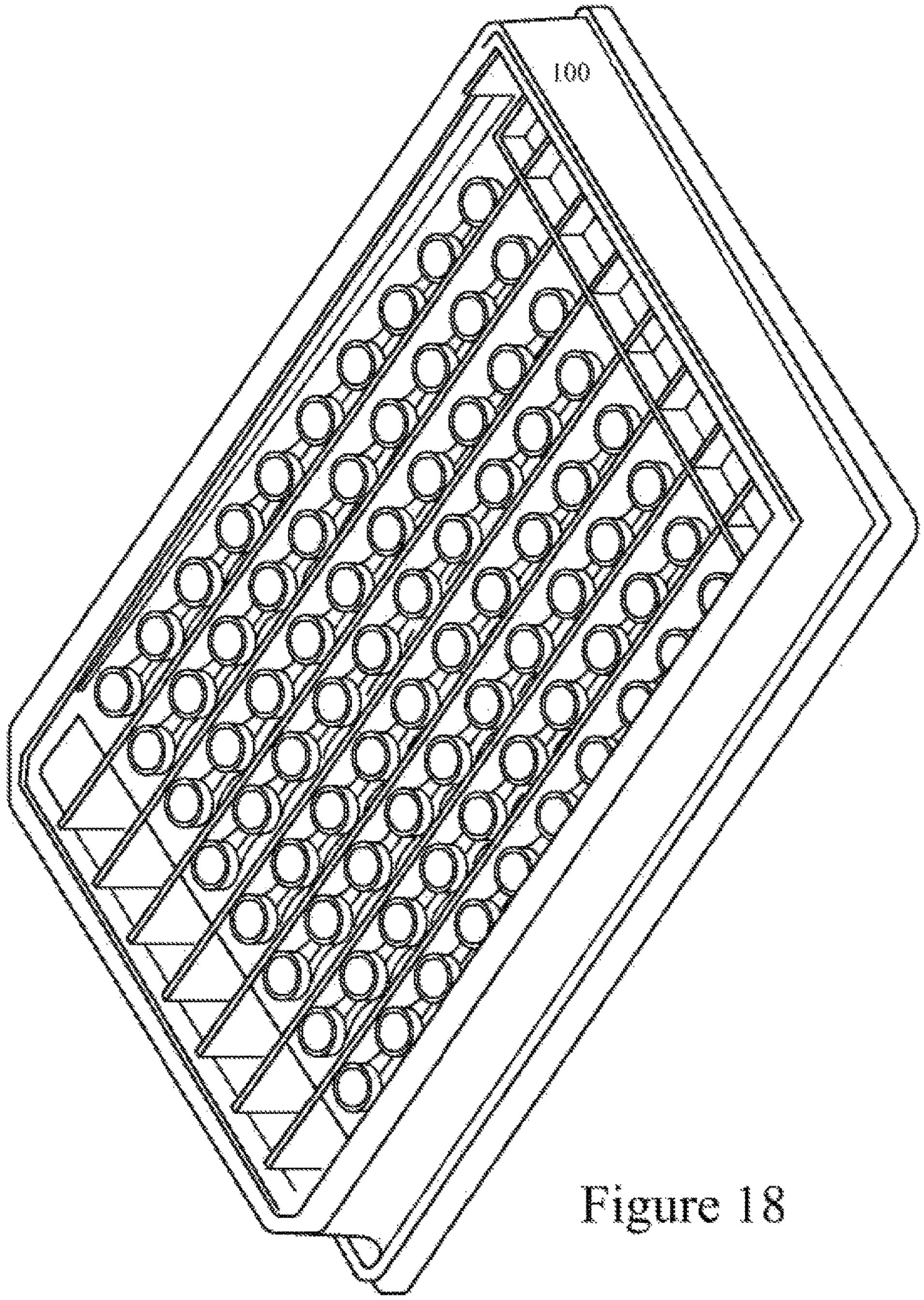
FIG. 18 shows a top view of the fluidics device in accordance with one or more embodiments of the present disclosure.
Figure 19:
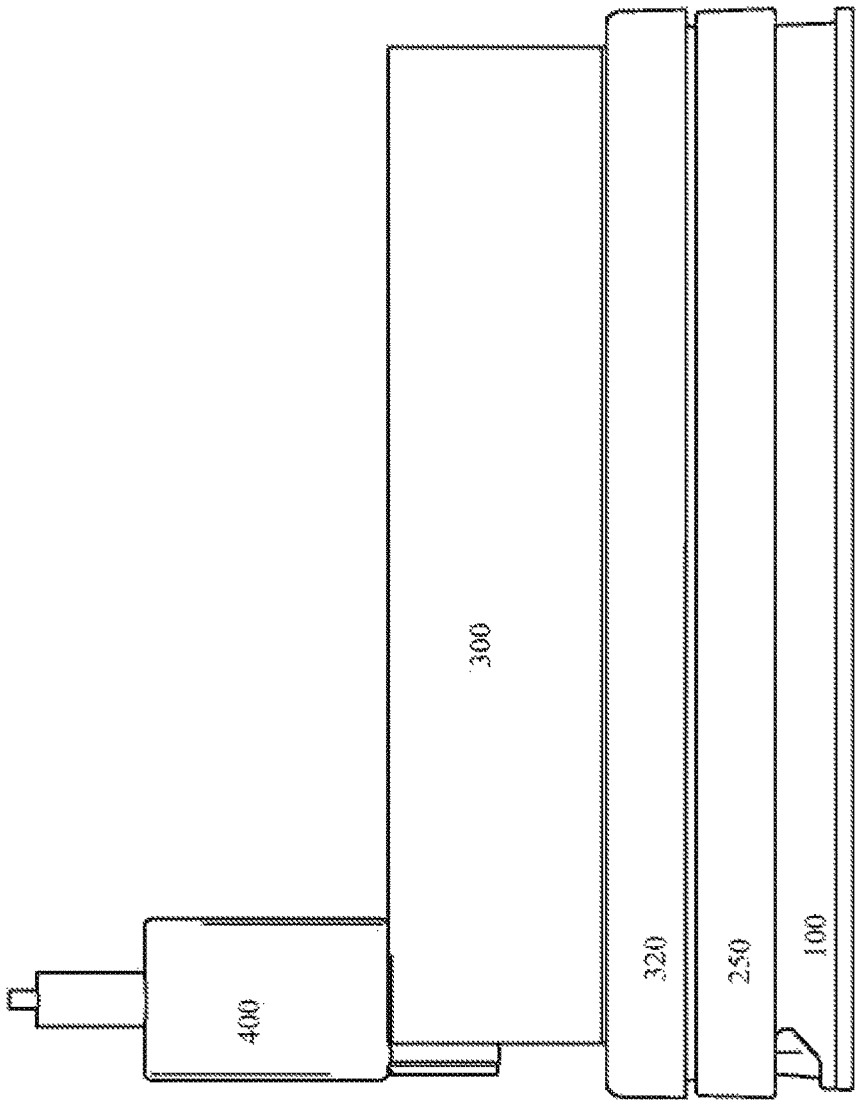
FIG. 19 shows a side view of the piston assembly engaged on top of the fluidics device in accordance with one or more embodiments of the present disclosure.
Figure 20:
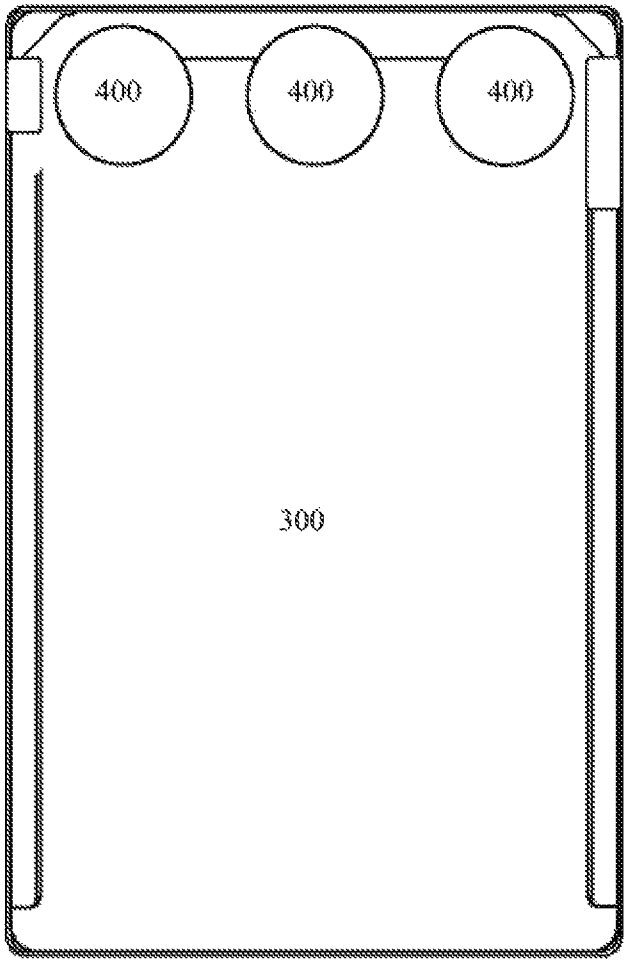
FIG. 20 shows a top view of the piston assembly including three solenoids in accordance with one or more embodiments of the present disclosure.
Figure 21:
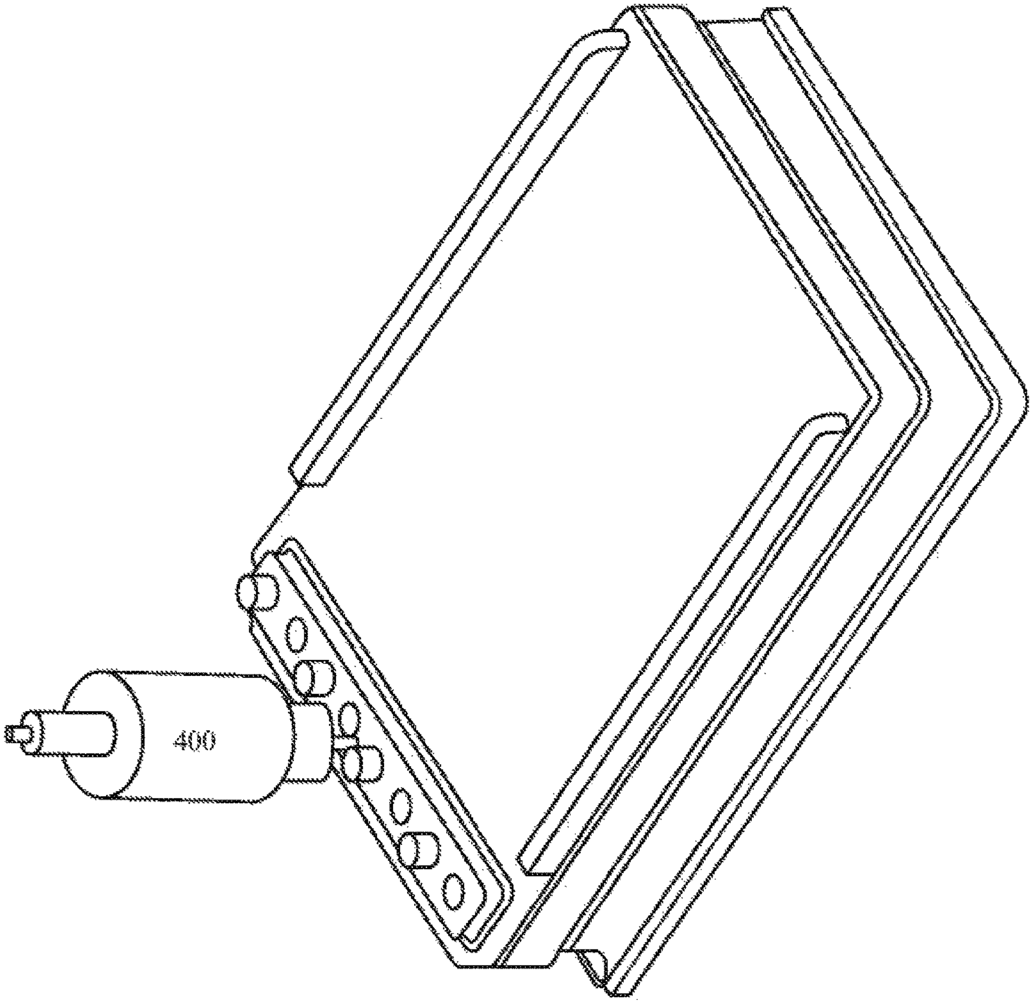
FIG. 21 shows an upward facing perspective of the piston assembly including one solenoid in accordance with one or more embodiments of the present disclosure.
Figure 22:
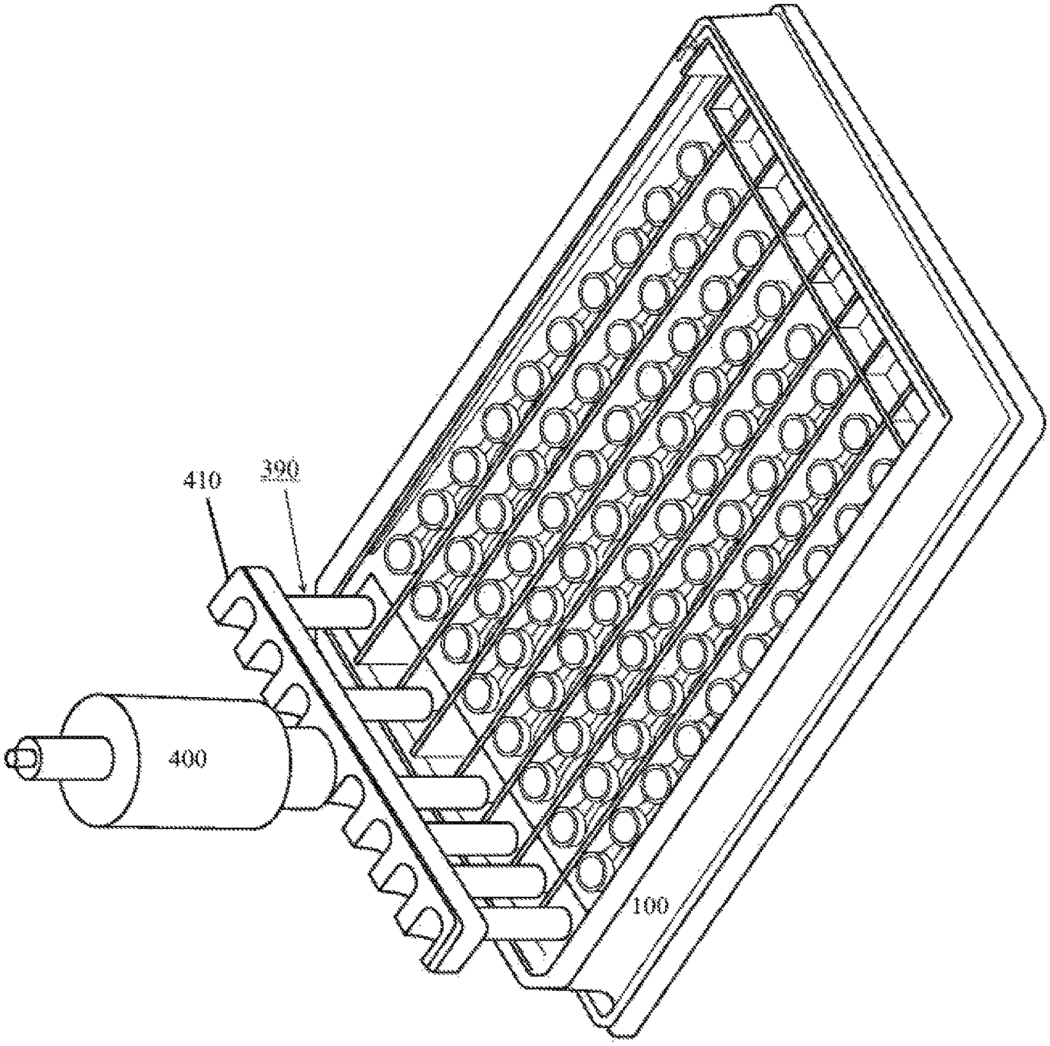
FIG. 22 shows an upward facing perspective of the fluidics device, pistons, a piston bar, and one solenoid in accordance with one or more embodiments of the present disclosure.
Figure 23:
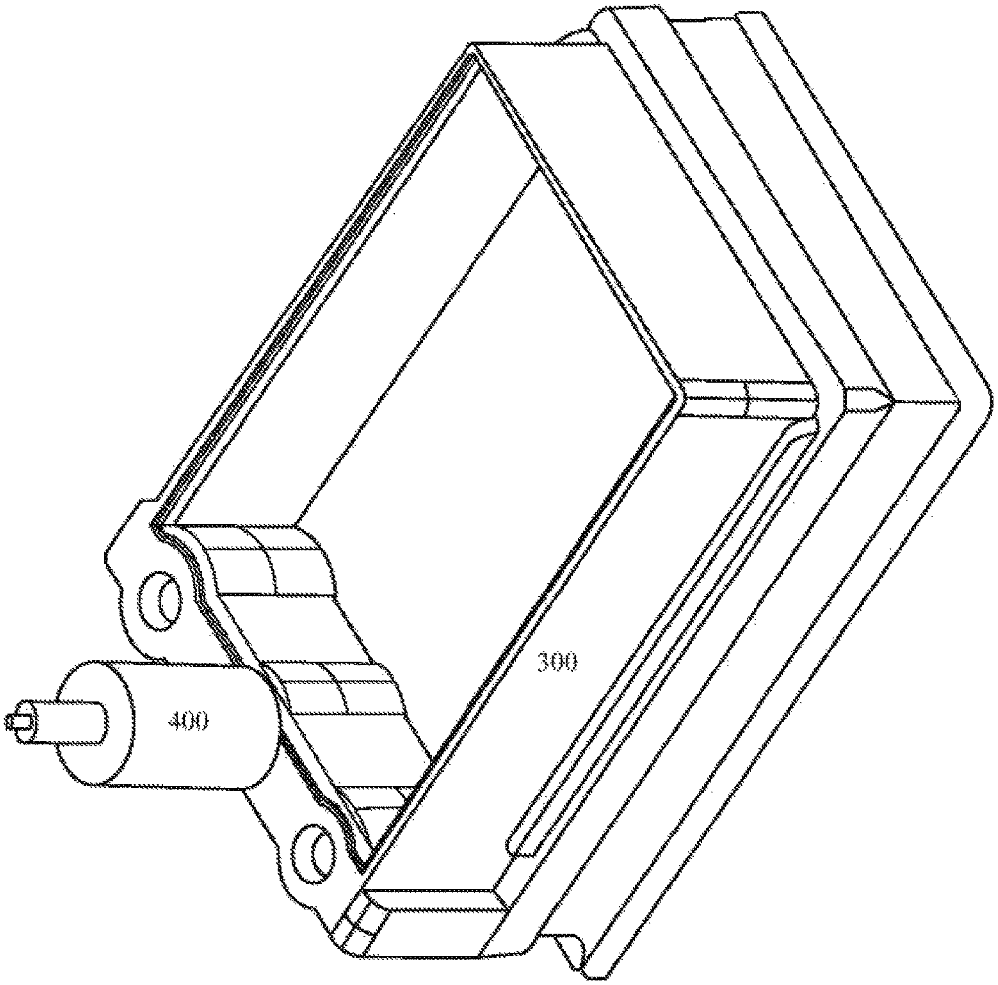
FIG. 23 shows an upward facing perspective of the solenoid and electronics unit in accordance with one or more embodiments of the present disclosure.
Figure 24:
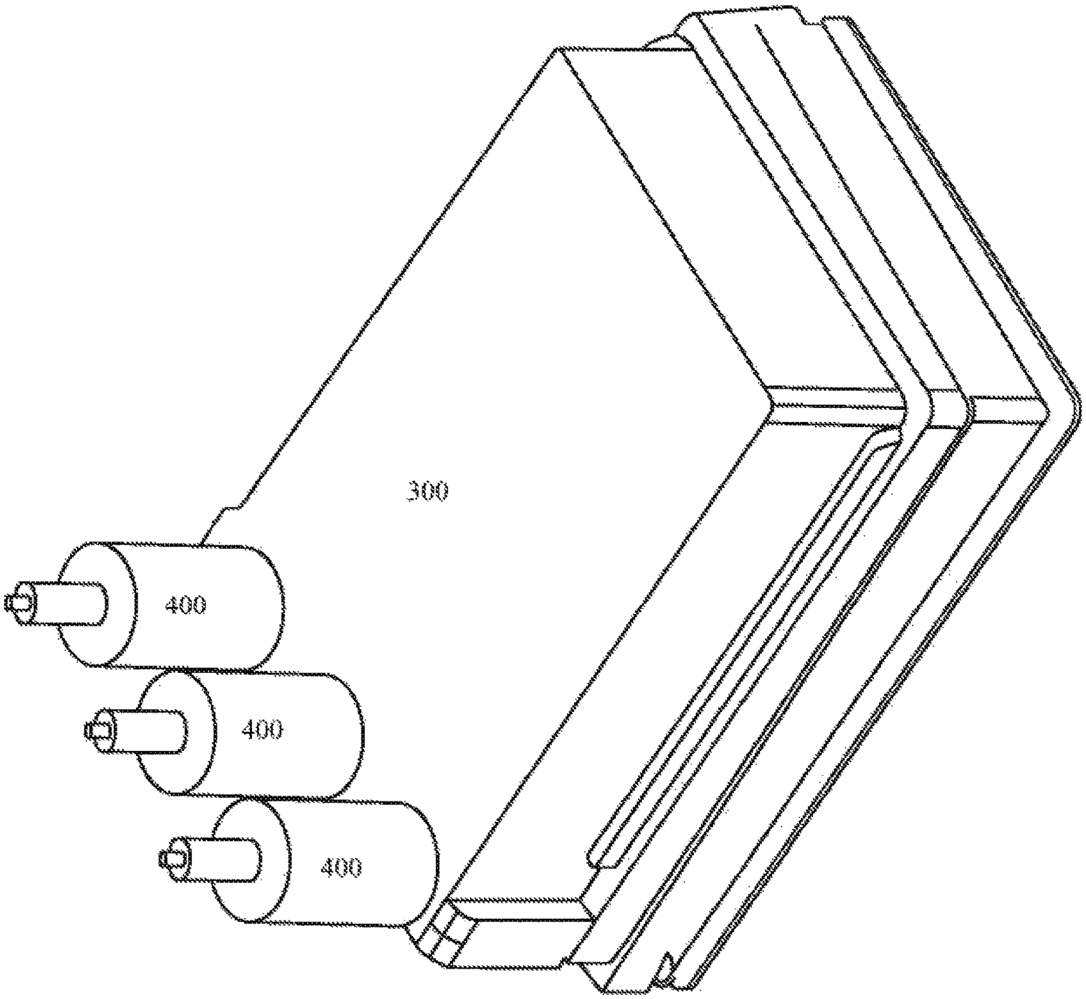
FIG. 24 shows an upward facing perspective of the piston assembly including solenoids in accordance with one or more embodiments of the present disclosure.

FIG. 16 shows a bottom perspective view of the piston assembly 300 engaged on top of the fluidics device 100 in accordance with one or more embodiments of the present disclosure. FIG. 17 shows a bottom view of the fluidics device 100 in accordance with one or more embodiments of the present disclosure. FIG. 18 shows a top view of the fluidics device 100 in accordance with one or more embodiments of the present disclosure. FIG. 19 shows a side view of the piston assembly 300 having a crank assembly 390, the piston assembly 300 engaged on top of the fluidics device 100 in accordance with one or more embodiments of the present disclosure. FIG. 20 shows a top view of the piston assembly 300 having a crank assembly 390 including three solenoids 400 in accordance with one or more embodiments of the present disclosure. FIG. 21 shows an upward facing perspective of the piston assembly 300 including one solenoid 400 in accordance with one or more embodiments of the present disclosure. FIG. 22 shows an upward facing perspective of the fluidics device 100, pistons 340, a piston bar 410, and one solenoid 400 in accordance with one or more embodiments of the present disclosure. FIG. 23 shows an upward facing perspective of the solenoid 400 and electronics unit 440 in accordance with one or more embodiments of the present disclosure. FIG. 24 shows an upward facing perspective of the piston assembly 300 including solenoids 400 in accordance with one or more embodiments of the present disclosure.

Figure 25:
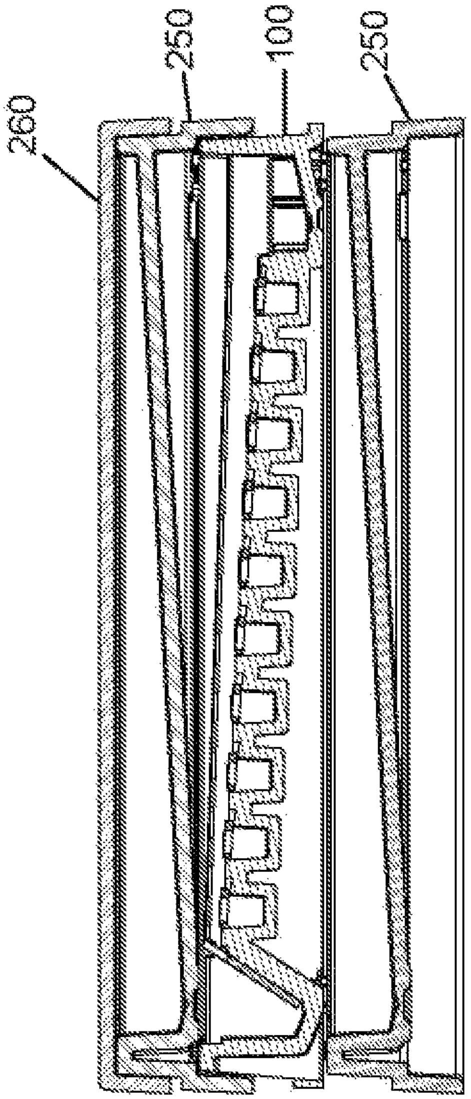
FIG. 25 shows a side view of the fluidics device of FIG. 1 as part of an assembly including a cover tray, a reservoir tray nestably engaged on top of the fluidics device, and a second reservoir tray nestably engaged underneath the fluidics device in accordance with embodiments of the present disclosure.

According to one or more embodiments of the presently disclosed subject matter, the overall assembly can further include a second reservoir tray 250 configured for nesting engagement underneath the fluidics device 100. FIG. 25 shows an exploded side view of this overall assembly including the second reservoir tray 250 in accordance with embodiments of the present disclosure. For this assembly, the fluidics device 100 can include the collection well 170 that is downstream from the plurality of wells 120 and the collection well 170 can define an aperture such that when the second reservoir tray 250 is in nesting engagement underneath the fluidics device 100, fluid from the collection well 170 of the fluidics device 100 flows through the aperture into the chamber 270 of the second reservoir tray 250. Referring to FIG. 25, the fluid can flow from the reservoir tray 250 nestably engaged on top of the fluidics device 100 from right to left through the aperture 280 of the reservoir tray 250 into the dosing well 110 of the fluidics device 100. The fluid can flow from the dosing well 110 from left to right through the aperture of the collection well 170 of the fluidics device 100 into the chamber 270 of the reservoir tray 250 nestably engaged underneath the fluidics device 100. The fluid can then flow in the second reservoir tray 250 from right to left.

According to one or more embodiments, the assembly can include one or more additional reservoir trays 250 configured for nesting engagement underneath the fluidics device 100.

According to one or more embodiments of the presently disclosed subject matter, the assembly can include a second fluidics device 100 configured for nesting engagement underneath the fluidics device 100. In this assembly, the fluidics device 100 can include the collection well 170 downstream from the plurality of wells 120 and the collection well 170 can define an aperture such that fluid from the collection well 170 flows through the aperture into the dosing well 110 of the second fluidics device 100 underneath when the fluidics devices 100 are nestably engaged.

Figure 26:
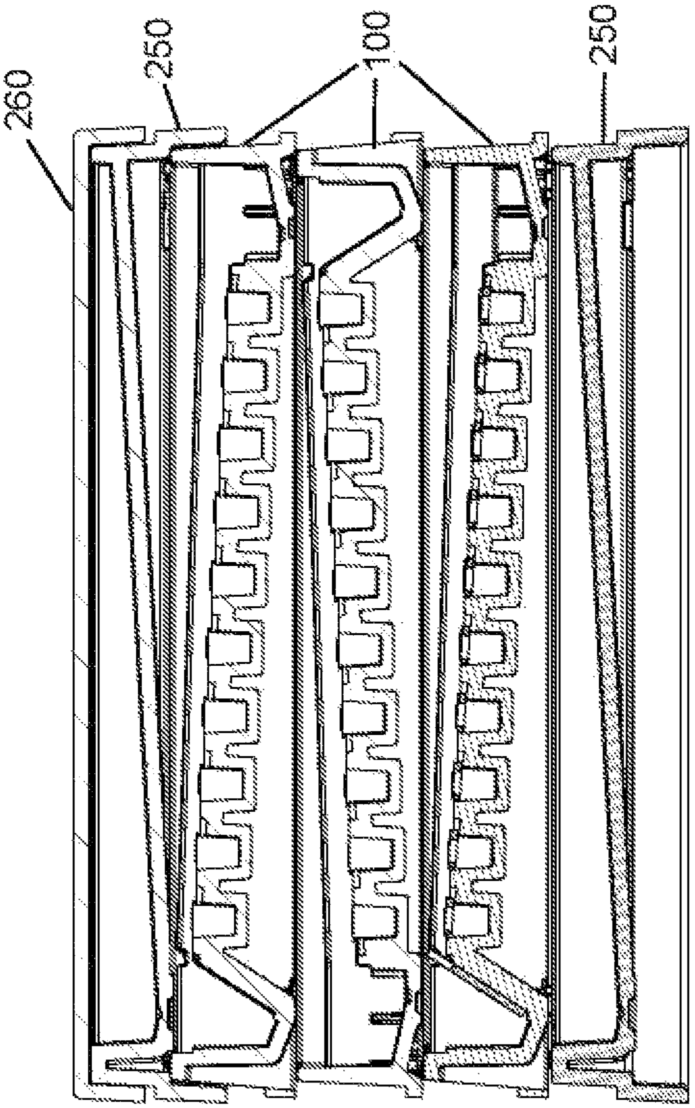
FIG. 26 shows a side view of the assembly of FIG. 25 further including two additional fluidics devices in nestable engagement in accordance with embodiments of the present disclosure.

According to one or more embodiments of the presently disclosed subject matter, the assembly can include one or more additional fluidics devices 100 configured for nesting engagement underneath the second fluidics device 100. The additional fluidics devices 100 can each include the collection well 170 downstream from the plurality of wells 120 and each collection well 170 can define an aperture such that fluid from the collection well 170 flows through the aperture into the dosing well 110 of the additional fluidics device 100 positioned underneath when the multiple fluidics devices 100 are nestably engaged. FIG. 26 shows an exploded side view of this assembly including a total of three fluidics devices 100 nestably engaged, reservoir trays 250 engaged on top of and underneath the three fluidics devices 100, and cover tray 260 engaged on top of the top reservoir tray 250 in accordance with embodiments of the present disclosure.

According to one or more embodiments of the presently disclosed subject matter, a method is provided for employing an assembly including one or more nestably engaged fluidics devices 100 and one or more reservoir trays 250 nestably engaged on top of and/or underneath the fluidics devices 100 as exemplified in FIGS. 8 and 25-26. The method can include adding a dosing fluid to the dosing well 120 and adding a respective host fluid to the plurality of wells 120 of the fluidics device(s) 100 such that the fluid is in fluid contact with the channel fluid flow path 130, whereby the dosing fluid flows to each of the respective host fluids in the plurality of wells 120 in a tempered manner. The method includes positioning the reservoir tray 250 above the fluidics device(s) 100 such that the reservoir tray 250 and the fluidics device(s) 100 are in nesting engagement, and adding the respective chamber fluid to the respective chamber 270 of the reservoir tray 250, whereby the respective chamber fluid flows into the dosing well 110 of the fluidics device 100 that is nestably engaged underneath the reservoir tray 250. In this manner, a larger supply of dosing fluid than can be contained by the dosing well 110 alone can be provided at a tempered rate to the one or more fluidics devices 100 that are nestably engaged underneath the reservoir tray 250.

According to one or more embodiments, the dosing fluid can include one or more of a drug, a legal or illegal drug, a toxin, an agent of warfare, a fragrance, a food spice, an oil, a gas, a metabolite, a compound, a hormone, a solution, a solute, a composite, a nutrient media, a differentiation media, or a growth media.

According to one or more embodiments, the plurality of wells 120 of the fluidics device 100 can contain a respective cell culture, whereby an effect of the tempered exposure to the dosing fluid on the cells can be measured. The effect of the tempered exposure to the dosing fluid on the cell cultures to be measured can be one or more of pharmacokinetics, drug metabolism, toxicity, pre-clinical pharmaceutical studies, cell response, cell receptor response, cell feedback signals, cell growth, cell death, cell differentiation, or cell regeneration. The respective cell culture can be a stem cell culture or a progenitor cell culture.

According to one or more embodiments, the method for employing the assembly can further include removing an aliquot of the respective host fluid from one or more of the plurality of wells 120 at one or more time periods to measure an effect of the dosing fluid from having been tempered through the plurality of wells 120. The plurality of wells 120 can contain a respective cell culture, and the method can include removing an aliquot of the respective host fluid from one or more of the plurality of wells 120 at one or more time periods to measure an effect of the dosing fluid on the cells.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

The invention claimed is:

1. A piston assembly comprising:

a reservoir tray configured for nesting engagement with a fluidics device and including:

a liquid chamber defining a chamber floor for containing a dosing fluid;

an aperture defined in the chamber floor and positioned above a dosing well of the fluidics device when the reservoir tray is nestably engaged with the fluidics device;

wherein the chamber floor is angled and the aperture is defined at a lower portion of the chamber floor such that the dosing fluid flows through the aperture into the dosing well of the fluidics device when the reservoir tray and the fluidics device are nestably engaged;

a reservoir cover defining a piston chamber that receives at least a portion of a piston for allowing the piston to translate between a first position a distance from the aperture and a second position proximal to the aperture; and a crank engaged with the piston for translating the piston between the first position and the second position such that the translation from the first position to the second position results in a portion of the dosing fluid flowing through the aperture to the dosing well when the reservoir tray and the fluidics device are nestably engaged.

2. The piston assembly of claim 1, wherein the aperture defines one or more openings, the one or more openings configured for communication with the dosing fluid in the liquid chamber such that surface tension of the dosing fluid maintains the dosing fluid in the liquid chamber until the piston is translated from the first position to the second position.

3. The piston assembly of claim 1, wherein the piston chamber defines a chamber lip for engaging with a piston catch defined by the piston, thereby retarding the translation of the piston when the piston translates from the second position to the first position.

4. The piston assembly of claim 1, wherein the reservoir cover defines a cover lip for engaging with a crank catch defined by the crank, thereby retarding the translation of the crank when the piston is translating from the second position to the first position.

5. The piston assembly of claim 1, wherein the chamber floor further defines a piston well including the aperture for receiving the piston in the second position and the dosing fluid.

6. The piston assembly of claim 5, wherein the piston well further includes a piston well wall for nestably engaging at least half of the circumference of the piston during the entire translation between the first position and the second position and for delivering the dosing fluid to the piston well.

7. The piston assembly of claim 6, wherein the chamber floor further defines a floor recess at the lower portion of the chamber floor proximal to the piston well and the piston well wall for receiving the dosing fluid and delivering the dosing fluid to the piston well.

8. The piston assembly of claim 1, wherein the crank includes a pin engaged within a piston channel defined in the piston for engaging the crank to the piston.

9. The piston assembly of claim 7, wherein the crank is in communication with a solenoid.

10. The piston assembly of claim 1, further comprising a fluidics device including:

a dosing well positioned upstream from a plurality of wells for containing a respective host fluid; and one or more channels extending between adjacent upstream and downstream wells to define a channel fluid flow path there between such that a dosing fluid deposited into the dosing well flows to the respective host fluid of the adjacent downstream well along the channel fluid flow path there between, and the respective host fluid subsequently flows to each adjacent downstream well along the channel fluid flow path there between.

11. The piston assembly of claim 10, wherein the fluidics device further includes:

a collection well downstream from the plurality of wells to collect the respective host fluid after its having flowed through the plurality of wells, wherein the collection well defines an aperture; and a second reservoir tray comprising at least one chamber for containing a respective chamber fluid and configured for nesting engagement underneath the fluidics device such that fluid from the collection well of the fluidics device flows through the aperture into the chamber of the second reservoir tray when the second reservoir tray and the fluidics device are nestably engaged.

12. The piston assembly of claim 10, further comprising:

a second fluidics device configured for nesting engagement underneath the fluidics device;

the fluidics device further including a collection well downstream from the plurality of wells to collect the respective host fluid after its having flowed through the plurality of wells;

wherein the collection well defines an aperture such that fluid from the collection well flows through the aperture into the dosing well of the second fluidics device when the fluidics devices are nestably engaged.

13. The piston assembly of claim 12, further comprising:

one or more additional fluidics devices configured for nesting engagement underneath the second fluidics device;

wherein the additional fluidics devices each comprise a collection well downstream from the plurality of wells to collect the respective host fluid after its having flowed through the plurality of wells;

wherein the collection well of each fluidics device defines an aperture such that fluid from the collection well flows through the aperture into the dosing well of the additional fluidics device positioned underneath when the fluidics devices are nestably engaged.

14. A piston assembly comprising:

a reservoir tray configured for nesting engagement with a fluidics device and including a liquid chamber defining a chamber floor and dividing walls creating subchambers for housing a dosing fluid, each of the subchambers having:

an aperture defined in the chamber floor and positioned above a dosing well of the fluidics device when the reservoir tray is nestably engaged with the fluidics device;

wherein the chamber floor is angled and the aperture is defined at a lower portion of the chamber floor such that the dosing fluid flows through the aperture into the dosing well of the fluidics device when the reservoir tray and the fluidics device are nestably engaged;

a reservoir cover defining a piston chamber housing a piston for each of the subchambers for allowing the piston to translate a between a first position a distance from the aperture and a second position proximal to the aperture; and a crank assembly engaged with the pistons for translating the pistons such that a portion of the dosing fluid flows through the aperture when the reservoir tray and the fluidics device are nestably engaged.

15. The piston assembly of claim 14, wherein the aperture defines one or more openings, the one or more openings configured for communication with the dosing fluid in the liquid chamber such that surface tension of the dosing fluid maintains the dosing fluid in the liquid chamber until the piston is translated from the first position to the second position.

16. The piston assembly of claim 14, wherein the piston chamber defines a chamber lip for engaging with a piston catch defined by the piston, thereby retarding the translation of the piston when the piston translates from the second position to the first position.

17. The piston assembly of claim 14, wherein the reservoir cover defines a cover lip for engaging with a crank catch defined by the crank assembly, thereby retarding the translation of the crank when the piston is translating from the second position to the first position.

18. The piston assembly of claim 14, wherein the chamber floor further defines a piston well including the aperture for receiving the piston in the second position and the dosing fluid.

19. The piston assembly of claim 18, wherein the piston well further includes a piston well wall for nestably engaging at least half of the circumference of the piston during the entire translation between the first position and the second position and for delivering the dosing fluid to the piston well.

20. The piston assembly of claim 18, wherein the chamber floor further defines a floor recess at the lower portion of the chamber floor proximal to the piston well and the piston well wall for receiving the dosing fluid and delivering the dosing fluid to the piston well.

21. The piston assembly of claim 14, wherein the crank assembly includes cranks, each crank engaged with the piston of each of the subchambers for translating the piston between the first position and the second position.

22. The piston assembly of claim 21, wherein each crank is in communication with a solenoid including a pin engaged with a piston channel defined by each piston.

23. The piston assembly of claim 14, wherein each piston defines a piston head and wherein the crank assembly includes a piston bar engaged with all of the piston heads for translating the pistons simultaneously between the first position and the second position.

24. The piston assembly of claim 23, wherein the crank assembly further includes at least one crank engaged with the piston bar for translating the piston bar, thereby translating the pistons between the first position and the second position.

25. The piston assembly of claim 24, wherein the at least one crank is in communication with at least one solenoid including a pin engaged with a piston bar channel defined by the piston bar.

26. The piston assembly of claim 14, further comprising a fluidics device including:

one or more dosing wells positioned upstream from a plurality of wells for containing a respective host fluid; and one or more channels extending between adjacent upstream and downstream wells to define a channel fluid flow path there between such that a dosing fluid deposited into the dosing well flows to the respective host fluid of the adjacent downstream well along the channel fluid flow path there between, and the respective host fluid subsequently flows to each adjacent downstream well along the channel fluid flow path there between.

* * * * *